United States Patent
Kono et al.

(10) Patent No.: US 8,616,062 B2
(45) Date of Patent: Dec. 31, 2013

(54) ULTRASONIC INSPECTION SYSTEM AND ULTRASONIC INSPECTION METHOD

(75) Inventors: Naoyuki Kono, Mito (JP); Isao Yoshida, Iwaki (JP); Masahiro Koike, Hitachi (JP); Yoshio Nonaka, Mito (JP); Hiroyuki Nakano, Mito (JP); Kenichi Otani, Hitachi (JP); Chihiro Matsuoka, Hitachi (JP); Masafumi Imai, Hitachiota (JP)

(73) Assignee: Hitachi-GE Nuclear Energy, Ltd., Ibaraki (JP)

( * ) Notice: Subject to any disclaimer, the term of this patent is extended or adjusted under 35 U.S.C. 154(b) by 350 days.

(21) Appl. No.: 13/028,268

(22) Filed: Feb. 16, 2011

(65) Prior Publication Data

US 2011/0197679 A1 Aug. 18, 2011

(30) Foreign Application Priority Data

Feb. 16, 2010 (JP) ................................. 2010-030891
Dec. 28, 2010 (JP) ................................. 2010-291697

(51) Int. Cl.
*G01N 29/06* (2006.01)

(52) U.S. Cl.
USPC ................................. 73/643; 73/649; 73/655

(58) Field of Classification Search
USPC ............ 73/643, 628, 634, 644, 649, 653, 655
See application file for complete search history.

(56) References Cited

U.S. PATENT DOCUMENTS

| | | | |
|---|---|---|---|
| 4,586,079 A * | 4/1986 | Cooper et al. | 348/82 |
| 4,856,354 A * | 8/1989 | Overbay | 73/866.5 |
| 5,107,709 A | 4/1992 | McCarty | |
| 5,475,613 A | 12/1995 | Itoga et al. | |
| 5,773,721 A | 6/1998 | Bashyam | |
| 6,666,094 B1 * | 12/2003 | Sauerland | 73/618 |
| 7,218,822 B2 * | 5/2007 | Treado et al. | 385/117 |
| 2009/0122008 A1 * | 5/2009 | Melkis et al. | 345/157 |
| 2013/0027716 A1 * | 1/2013 | Melkis et al. | 356/614 |

FOREIGN PATENT DOCUMENTS

| | | |
|---|---|---|
| JP | 61-65350 U | 5/1986 |
| JP | 63-269054 A | 11/1988 |
| JP | 1-127952 A | 5/1989 |
| JP | 4-218766 A | 8/1992 |
| JP | 6-102258 A | 4/1994 |
| JP | 06-64152 | 9/1994 |
| JP | 10-19858 A | 1/1998 |
| JP | 2002-90253 A | 3/2002 |
| JP | 2005-43139 A | 2/2005 |
| JP | 2005-300363 A | 10/2005 |
| JP | 2006-133122 A | 5/2006 |
| JP | 2006-308338 A | 11/2006 |
| JP | 2009-222642 A | 10/2009 |
| JP | 2010-32434 A | 2/2010 |

OTHER PUBLICATIONS

JP Office Action in JP App. No. 2010-030891, dated Jul. 23, 2013.

* cited by examiner

*Primary Examiner* — J M Saint Surin
(74) *Attorney, Agent, or Firm* — Mattingly & Malur, PC

(57) ABSTRACT

In an ultrasonic inspection method or ultrasonic inspection system in which an ultrasonic wave is propagated to an test object via a medium such as a liquid or a gas, an incident position of the ultrasonic wave is accurately and reliably identified. In an ultrasonic inspection method based on an immersion technique, an optical irradiator is mounted on an ultrasonic wave transmitting/receiving unit, an optical marker is irradiated from the optical irradiator to the test object, and an irradiated position of the optical marker is imaged using imaging equipment in order to perform inspection.

15 Claims, 31 Drawing Sheets

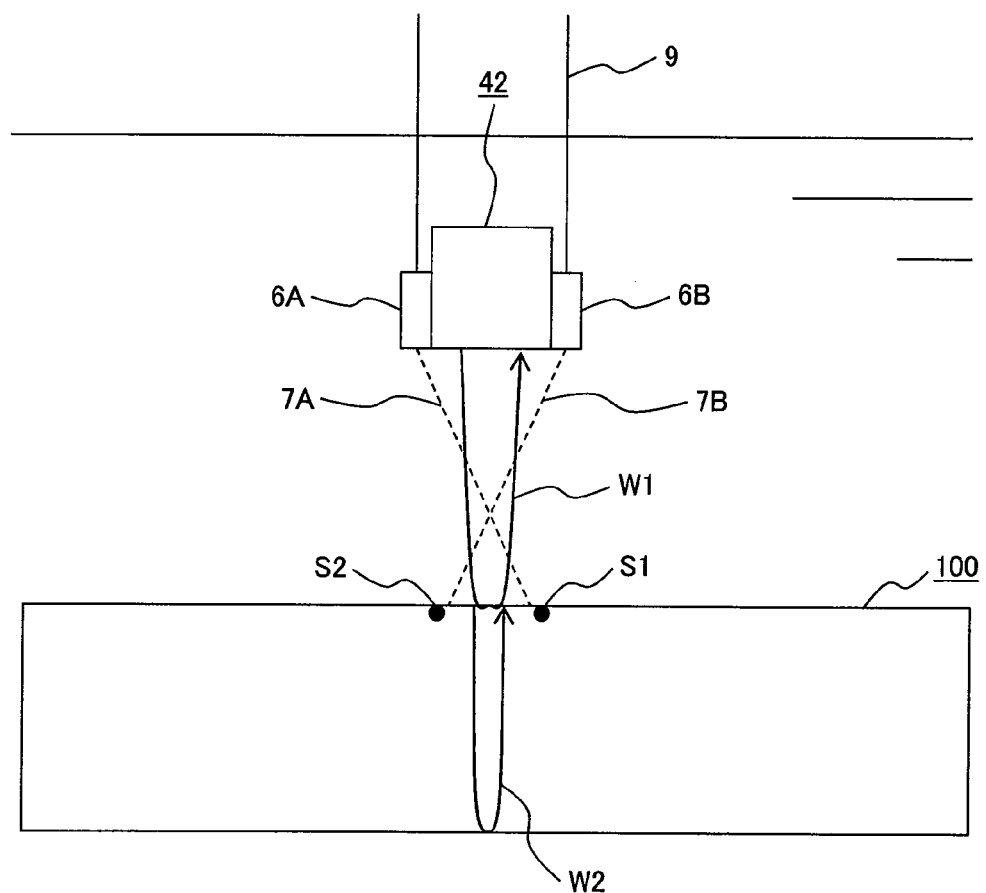

ULTRASONIC INSPECTION SYSTEM AND ULTRASONIC INSPECTION METHOD

CLAIM OF PRIORITY

The present application claims priority from Japanese Patent Application No. 2010-030891 filed on Feb. 16, 2010 and No. 2010-291697 filed on Dec. 28, 2010, the content of which are hereby incorporated by reference into this application.

BACKGROUND OF THE INVENTION

1. Field of the Invention

The present invention relates to an ultrasonic inspection system and ultrasonic inspection method based on an immersion technique for performing inspection with a liquid such as water interposed between an ultrasonic sensor and an test object.

2. Description of the Related Art

A welded part of a structure has a possibility that various defects may occur therein. As a nondestructive inspection technique to be applied for the interior of the welded part or the internal surface thereof that is inaccessible to a person or an apparatus, an ultrasonic inspection method has been widely adopted. When the surface of the welded part has irregularities or an ultrasonic sensor cannot be brought into direct contact with the surface of the welded part because of the narrowness, ultrasonic inspection based on an immersion technique of separating the ultrasonic sensor from the test object by a certain space and filling the space with a liquid such as water or oil is adopted.

For the conventional ultrasonic inspection based on the immersion technique, an ultrasonic inspection system has been proposed. As described in patent document 1 (JP-A-2005-300363), the ultrasonic inspection system includes a computer-aided design (CAD) device that displays the position of a probe, an incident direction of an ultrasonic wave, and a trajectory of the ultrasonic wave on the basis of information on the shape of a inspection surface, a scanner that positions the probe by making three-dimensional movements, the probe, and a distance sensor that measures a distance from the inspection surface.

According to the proposed ultrasonic inspection system, even if the inspection surface has irregularities or a crack, an optimal probe position is detected and the probe can be moved to the optimal position by the scanner.

Patent document 2 (JP-A-2005-43139) has disclosed a laser ultrasonic inspection apparatus in which a laser light source 1 is used to cause an ultrasonic wave to occur in a member to be inspected, and a laser light source 2 and a light condenser are used to optically detect an ultrasonic signal.

Patent document 3 (JP-A-2009-222642) has disclosed an ultrasonic inspection apparatus that includes an ultrasonic probe and a charge-coupled device (CCD) camera and uses the CCD camera to check an ultrasonic wave incident position.

Further, patent document 4 (JP-A-10-19858) has disclosed an ultrasonic inspection apparatus that records ultrasonic images of an test object and appearance information acquired by a digital camera.

For assessment of the integrity of a structure, an ultrasonic inspection method is widely adopted as a nondestructive inspection technique for the surface of the structure or the interior thereof. When the surface of the structure that is test object has irregularities or curvature or when an ultrasonic sensor cannot be brought into direct contact with the structure because of the narrowness of a space near the structure, such ultrasonic inspection is adopted that: the space between the ultrasonic sensor and test object is filled with a medium (couplant) such as a liquid or a gas which permits propagation of an ultrasonic wave; and the structure is inspected via the medium. For example, when water that is a liquid is used as the medium, the ultrasonic inspection is called an immersion technique. When air that is a gas is adopted as the medium, the ultrasonic inspection is called an airborne ultrasonic wave flow detection method. Thus, the ultrasonic inspection is called differently depending on the medium.

A technique of implementing ultrasonic inspection via a medium is such that inspection is performed by separating an test object from an ultrasonic sensor by a predetermined distance (for example, about several centimeters in the case of the immersion technique) as multiply-reflected waves of an ultrasonic wave may affect a inspection signal in the medium. Therefore, the position of the ultrasonic sensor and a point (ultrasonic wave incident position) on an test object which the ultrasonic wave incidents after propagating through the medium have a spatial distance between them. In order to obtain a more highly reliable result of inspection, it is necessary to accurately grasp the positional relationship between the ultrasonic sensor and test object, or more particularly, the ultrasonic wave incident position on the test object.

For example, in relation to the conventional ultrasonic inspection, an ultrasonic inspection apparatus combined with imaging equipment has been disclosed in patent document 5 (JP-A-2010-32434). Herein, a method implemented as a conventional method of identifying an ultrasonic wave incident position is such that: an image of an object of testing is picked up using a video camera; reflection of an ultrasonic wave is detected while coordinates representing the position of an ultrasonic probe are measured using the camera; and a inspection image obtained based on an ultrasonic reflected wave and a camera image are displayed while being superposed on each other.

Further, patent document 6 (JP-A-6-102258) has disclosed an ultrasonic inspection method and system in which: a laser or an LED attached to an ultrasonic probe is imaged using a camera in order to find out a three-dimensional shape of an object of inspection; and a three-dimensional graphic image is produced and displayed while being superposed on an ultrasonic inspection screen image.

The foregoing techniques have been devised on the assumption that a direct contact technique of bringing an ultrasonic sensor into contact with an test object is adopted. The patent documents describe the methods, apparatuses, and systems that identify the position of the ultrasonic sensor. However, as long as an immersion technique or any other ultrasonic inspection method in which the position of the ultrasonic sensor and an ultrasonic wave incident position are inconsistent with each other and a medium is employed is adopted, the incident position cannot be identified.

SUMMARY OF THE INVENTION

According to the aforesaid related art, a distance sensor is used to measure a shape, and an incident position of an ultrasonic wave or an incident direction thereof is analyzed in order to find out an optimal probe position. However, a technique for verifying whether an ultrasonic wave actually incidents an intended position has not been devised. Anyhow, the related art is not satisfactory enough to verify whether the ultrasonic wave accurately incidents the intended position.

Accordingly, an object of the present invention is to provide a novel ultrasonic inspection system capable of accurately checking an ultrasonic wave incident position according to an ultrasonic inspection method based on an immersion technique, and the ultrasonic inspection method.

The present invention provides an ultrasonic inspection system that is employed in ultrasonic inspection of an test object based on an immersion technique, and that includes an ultrasonic sensor which emits or receives an ultrasonic wave, an ultrasonic inspection device which displays information on a result of inspection, a drive unit which is remotely controlled in order to move the ultrasonic sensor to a predetermined position on the test object, a laser that irradiates a laser beam to the test object, and imaging equipment that images the test object and a laser beam irradiated position. The imaging equipment is a camera.

In the ultrasonic inspection system, the ultrasonic sensor includes at least two lasers, and the optical axes of the lasers are tilted toward each other so that visible laser beams can intersect at a position separated by a predetermined distance from the ultrasonic wave emitting surface of the ultrasonic sensor.

In the ultrasonic inspection system, the distance to a position at which the visible laser beams intersect is squared with a water distance required for an ultrasonic wave, which is emitted from the ultrasonic sensor, to incident the test object.

In the ultrasonic inspection system, the ultrasonic sensor includes an array transducer that controls delay times of ultrasonic waves generated by plural transducers so as to perform inspection.

The imaging equipment is realized with a fiberscope that includes an illumination light source and a camera and images an test object. As the ultrasonic sensor, an array transducer that controls delay times of ultrasonic waves, which are generated by plural transducers, so as to perform inspection is adopted.

Further, in an ultrasonic inspection method based on an immersion technique, an ultrasonic sensor and a laser are mounted in a drive unit that is remotely controlled for driving. A visible laser beam is irradiated from the laser to an test object. Imaging equipment is used to image an irradiated position of the visible laser beam for the purpose of inspection. Further, the imaging equipment is a camera.

Further, in the ultrasonic inspection method, the ultrasonic sensor includes at least two lasers. The optical axes of the lasers are tilted toward each other so that the visible laser beams can intersect at a position separated by a predetermined distance from the ultrasonic wave emitting surface of the ultrasonic sensor.

Further, in the ultrasonic inspection method, a distance to a position at which the visible laser beams intersect is squared with a water distance required for an ultrasonic wave, which is emitted from the ultrasonic sensor, to incident an test object.

Further, in the ultrasonic inspection method, an ultrasonic sensor and a fiberscope are mounted in a drive unit that is remotely controlled for driving. The fiberscope is used to image an ultrasonic wave emitting direction in order to perform inspection.

Further, the present invention is accomplished by another ultrasonic inspection system that propagates an ultrasonic wave to an test object via a medium such as a liquid or a gas. The ultrasonic inspection system includes an ultrasonic wave transmitting/receiving unit that transmits or receives an ultrasonic wave, an acoustic image display device that displays information on a result of inspection, an optical irradiator that is mounted on the ultrasonic wave transmitting/receiving unit and irradiates an optical marker to the test object, imaging equipment that images the test object and an irradiated position of the optical marker, and an optical image display device that displays an image picked up by the imaging equipment.

According to the present system, the optical marker irradiated to the test object from the optical irradiator mounted on the ultrasonic wave transmitting/receiving unit is imaged by the imaging equipment. Thus, an incident position on the test object of an ultrasonic wave or an occurring position on the test object of an ultrasonic wave to be received can be obtained.

In the ultrasonic inspection system, the imaging equipment may be mounted on the ultrasonic wave transmitting/receiving unit. According to the present system, an acoustic image produced by the ultrasonic wave transmitting/receiving unit and an optical image picked up by the imaging equipment can visualize a range covering the same region in the test object. An incident position or an occurring position on the test object of an ultrasonic wave can be readily identified.

In the ultrasonic inspection system, the ultrasonic wave transmitting/receiving unit may include plural optical irradiators. Optical markers irradiated from the optical irradiators may intersect at a position separated by a predetermined distance from the ultrasonic wave emitting surface of the ultrasonic sensor. According to the present system, the distance between the ultrasonic sensor and test object can be obtained. Eventually, an incident position or an occurring position on the test object of an ultrasonic wave to be received can be more accurately obtained.

In the ultrasonic inspection system, a distance to the position at which the optical markers intersect may be squared with a distance between the ultrasonic wave transmitting/receiving unit and test object.

In the ultrasonic inspection system, an array transducer that controls delay times of ultrasonic waves, which are generated by plural transducers, so as to perform inspection may be adopted as the ultrasonic wave transmitting/receiving unit for either or both of transmitting and receiving purposes. According to the present system, since the directions of ultrasonic waves transmitted or received by the array transducer can be electronically controlled, the ultrasonic wave transmitting/receiving unit can be readily aligned with the test object.

In the ultrasonic inspection system, the imaging equipment may be a camera having a lens, and may include a unit that outputs an image dependent on the power of the lens. According to the present system, an optical image showing an test object and an irradiated position of an optical marker can be used to obtain a distance to the object of imaging. Eventually, an incident position of an ultrasonic wave or an occurring position on the test object of an ultrasonic wave to be received can be more accurately obtained.

In the ultrasonic inspection system, a unit that synthesizes an acoustic image and an optical image may be included. According to the present system, the acoustic image produced by the ultrasonic wave transmitting/receiving unit and the optical image picked up by the imaging equipment can visualize a range covering the same region of an test object, and can be synthesized and displayed. Eventually, an incident position or an occurring position on the test object of an ultrasonic wave to be received can be readily identified.

Further, the present invention is accomplished by another ultrasonic inspection method of propagating an ultrasonic wave to an test object via a medium such as a liquid or a gas. According to the ultrasonic inspection method, an ultrasonic wave is transmitted to the test object, and a reflected wave from the surface or interior of the test object is received as a receiving signal. A result of inspection represented by the receiving signal is displayed as an acoustic image. An optical marker is irradiated from an optical irradiator, which is mounted on an ultrasonic wave transmitting/receiving unit, to the surface of the test object. Imaging equipment is used to image the test object and optical marker. The pickup image is displayed as an optical image in order to perform inspection.

According to the foregoing method, the optical marker irradiated from the optical irradiator, which is mounted on the ultrasonic wave transmitting/receiving unit, to the test object is imaged by the imaging equipment. Therefore, an incident position on the test object of an ultrasonic wave or an occurring position on the test object of an ultrasonic wave to be received can be identified in order to perform ultrasonic inspection.

In the ultrasonic inspection method, the imaging equipment may be used to inspect the surface of the test object. An optical inspection and an ultrasonic inspection may be carried out simultaneously or selectively. According to the present method, an acoustic image produced by the ultrasonic wave transmitting/receiving unit and an optical image picked up by the imaging equipment can visualize a range covering the same region of the test object, and can be selectively displayed or simultaneously displayed as a synthetic image. While the integrity of the test object is checked through a surface inspection, an incident position of an ultrasonic wave or an occurring position on the test object of an ultrasonic wave to be received can be identified. Eventually, the reliability of the inspection can be improved.

In the ultrasonic inspection method, the ultrasonic wave transmitting/receiving unit may include plural optical irradiators. The optical axes of the optical irradiators may be tilted toward one another so that shapes of optical markers can intersect. The shape of each of the optical markers on the surface of an test object may be a spot. When the optical markers intersect at one point, a distance between the ultrasonic wave transmitting/receiving unit and test object may be identified. According to the present method, the distance between an ultrasonic sensor and the test object can be obtained. Eventually, an incident position or an occurring position on the test object of an ultrasonic wave to be received can be more accurately obtained.

In the ultrasonic inspection method, the ultrasonic wave transmitting/receiving unit may include plural optical irradiators. The shape of each of optical markers on the surface of an test object may be a line. The optical irradiators may be arranged so that the optical markers can intersect. An angle at which the ultrasonic wave transmitting/receiving unit is disposed with respect to the test object may be identified based on the directions of the lines of the optical markers irradiated to the test object. According to the present method, the angle at which the ultrasonic sensor is disposed with respect to the test object can be obtained. Eventually, an incident position or an occurring position on the test object of an ultrasonic wave to be received can be more accurately obtained.

In the ultrasonic inspection method, the plural optical irradiators mounted on the ultrasonic wave transmitting/receiving unit may project optical markers according to any of plural irradiation patterns. According to the present method, the plural optical markers can be readily identified, and a human error can be prevented. Eventually, an incident position or an occurring position on an test object of an ultrasonic wave to be received can be more accurately obtained.

According to the present invention, a visible laser beam is irradiated to an incident position of an ultrasonic wave emitted from an ultrasonic sensor, and the surface of an test object which the ultrasonic wave incidents is monitored using imaging equipment such as a camera. Accordingly, a deviation from a region to be inspected due to an incorrect manipulation performed in order to sweep the ultrasonic sensor, or a human error such as an erroneous decision made on a detected ultrasonic image (echo) can be avoided. While the incident position of the ultrasonic wave emitted from the ultrasonic sensor is imaged, inspection is carried out. Therefore, if a doubt of a defect is demonstrated by a result of inspection, a situation of inspection encompassing information on the surface of the test object at the position concerned can be checked. Eventually, a defect deciding ability and precision in dimension measurement can be improved.

According to the present invention, an optical marker is irradiated to an test object, and the surface of the test object which an ultrasonic wave incidents is imaged by imaging equipment such as a camera. Thus, even when a complex shape is inspected or an inspection is performed through remote control, an incident position of an ultrasonic wave, which is emitted from an ultrasonic wave transmitting/receiving unit, on an actual test object, or an occurring position on the test object of an ultrasonic wave to be received can be identified owing to the optical marker. Therefore, a highly reliable ultrasonic inspection can be provided.

Further, while an test object as well as an incident position of an ultrasonic wave emitted from an ultrasonic wave transmitting/receiving unit is being imaged, inspection is implemented. Therefore, if a doubt of a defect is demonstrated by a result of ultrasonic inspection, a situation of inspection encompassing information on the surface of the test object at the incident position of the ultrasonic wave emitted from the ultrasonic wave transmitting/receiving unit, which is identified with an optical marker, can be checked. Otherwise, when the doubt of a defect derives from visual inspection based on imaging, the result of ultrasonic inspection obtained at the position concerned can be checked. Therefore, a defect deciding ability and precision in dimension measurement can be improved more greatly than they conventionally can be.

BRIEF DESCRIPTION OF THE DRAWINGS

FIG. 7 is an illustrative diagram showing a case where the number of irradiated positions of visible laser beams in the embodiment 2 is two;

DESCRIPTION OF THE PREFERRED EMBODIMENTS

Figure 1:
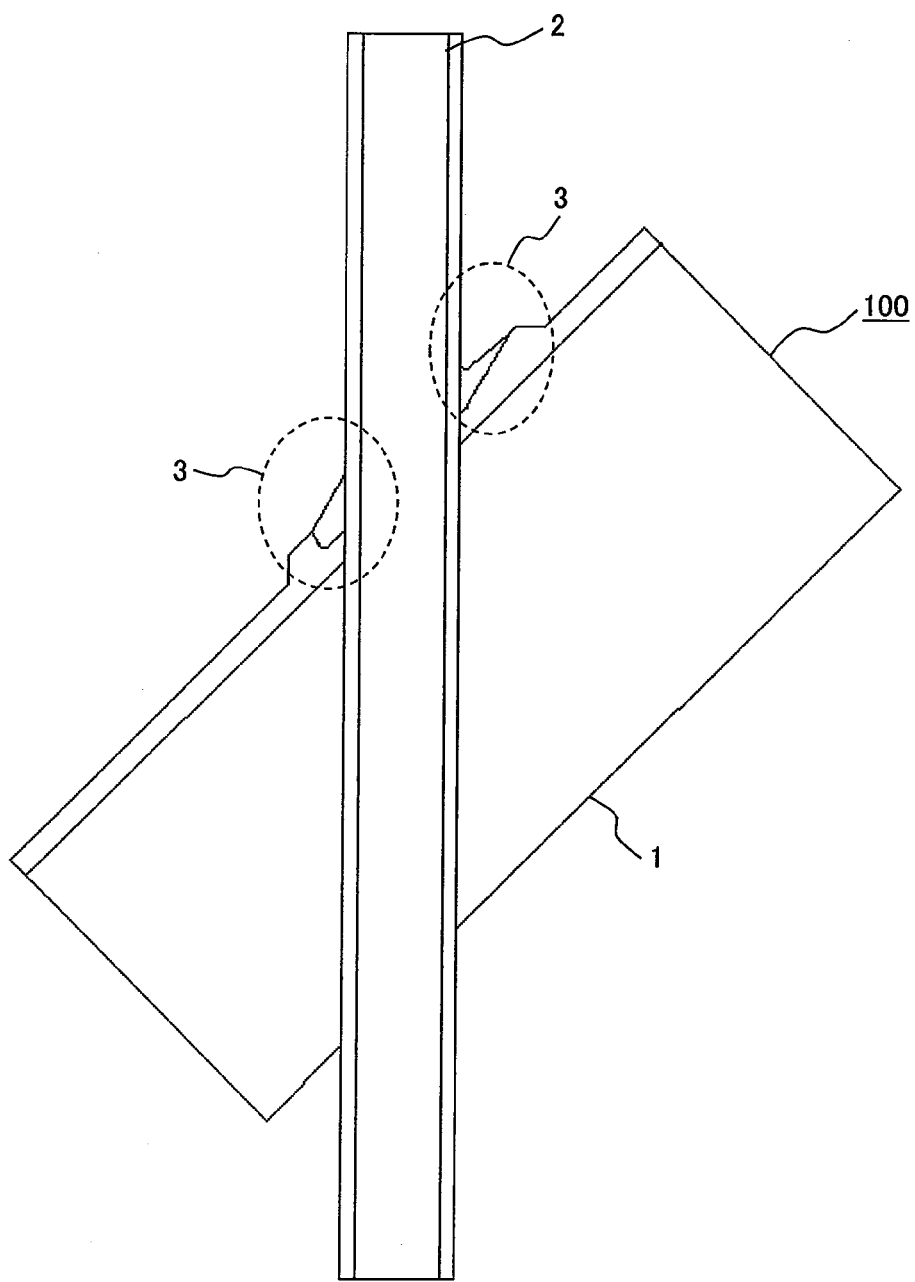
FIG. 1 is a sectional view of an test object to which the present invention is adapted.

FIG. 1 is a sectional view of an test object 100 having a pipe 2 penetrated through a steel plate 1, to which the present invention is adapted, at a predetermined angle. The periphery of the pipe 2 is welded to form a welded part 3. The presence or absence of a flaw in the welded part 3 is inspected through ultrasonic inspection based on an immersion technique. The shape of the welded part 3 three-dimensionally varies depending on an angle of the circumferential direction of the pipe 2. The welded part 3 on the soaring side of the steel plate is the narrowest, and has a shape making it difficult to accurately route an ultrasonic wave to an intended position.

Figure 2:
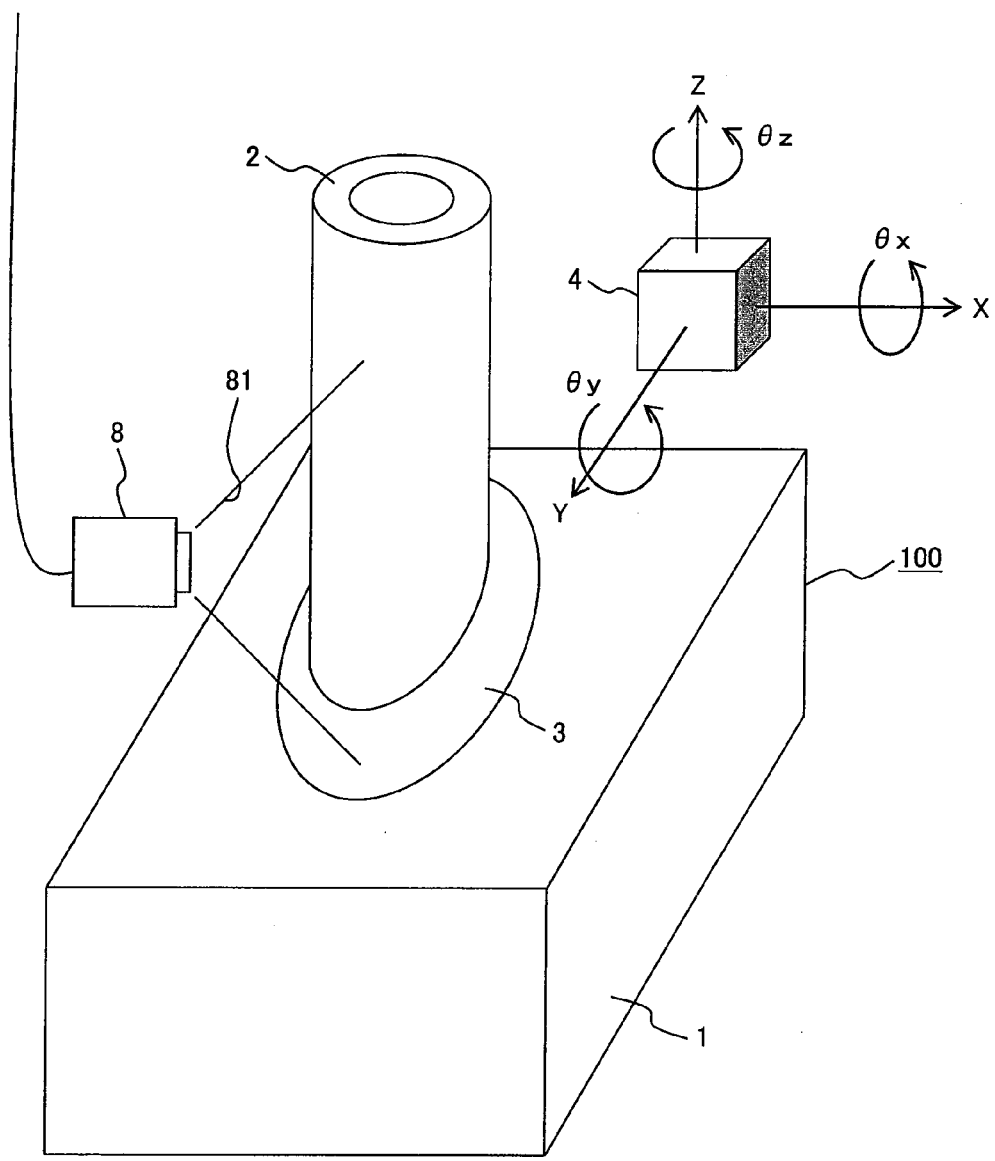
FIG. 2 is an illustrative diagram showing a configuration of an ultrasonic inspection system.

FIG. 2 is an illustrative diagram showing a configuration of an ultrasonic inspection system, and illustratively shows movements of an ultrasonic sensor 4 included in the ultrasonic inspection system. In order to sweep the ultrasonic sensor 4, a drive unit capable of moving in axial directions X, Y, and Z and rotating directions θx, θy, and θz with the ultrasonic sensor 4 itself as a center, for example, a manipulator employed in a robot or the like for controlling six or more axes is prepared. Reference numeral 8 denotes a camera that images an ultrasonic wave incident part of an test object, and reference numeral 81 denotes a viewing angle of the camera. The ultrasonic inspection system further includes a display device that is not shown and displays information on a result of inspection, and a recording unit that records the result of inspection.

Embodiment 1

Figure 3:
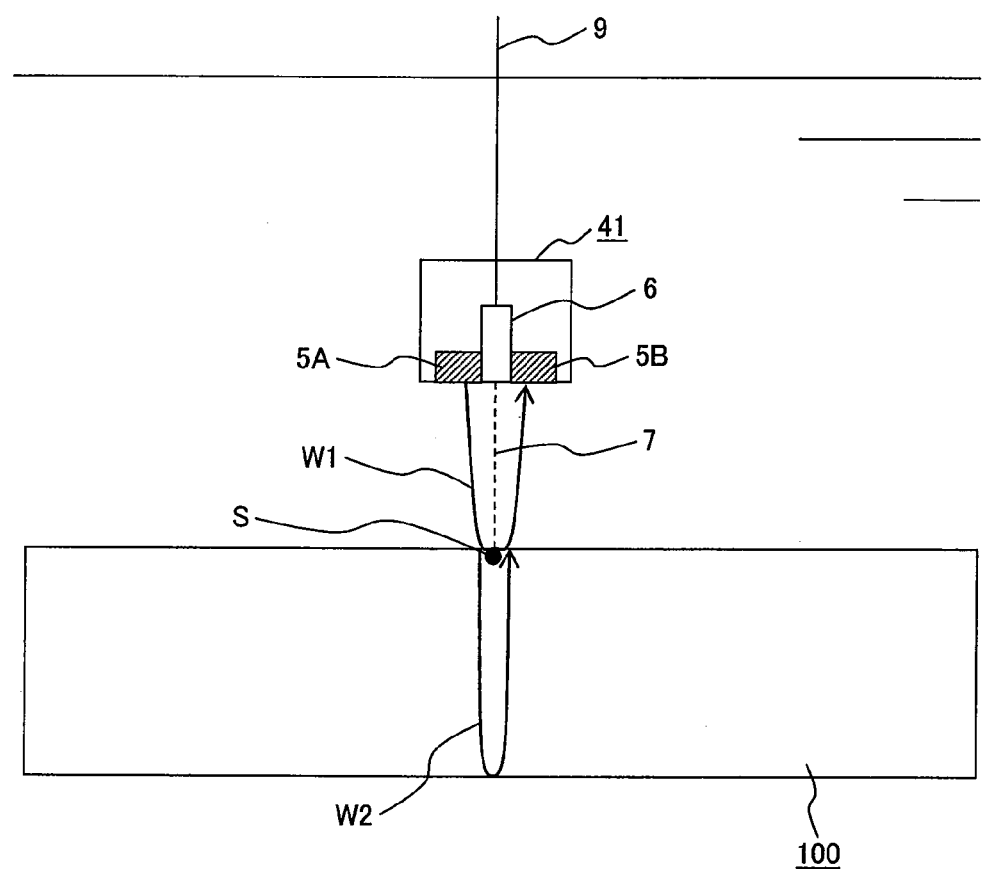
FIG. 3 is an illustrative diagram showing an ultrasonic sensor included in an embodiment 1 of the present invention.

FIG. 3 shows a configuration of an ultrasonic sensor included in an ultrasonic inspection system in accordance with an embodiment 1 of the present invention. A laser 6 that generates a visible laser beam 7 is incorporated in the ultrasonic sensor 41. The ultrasonic sensor 41 further includes an ultrasonic wave transmitter 5A and an ultrasonic wave receiver 5B. Symbol S denotes an incident position on an test object of an ultrasonic wave, W1 denotes a surface reflection ultrasonic wave of an incident ultrasonic wave, and W2 denotes an internally reflected ultrasonic wave. The units are immersed in water that is an ultrasonic medium. Reference numeral 9 denotes a cable. The cable 9 bears the ultrasonic sensor 41 and includes a power cable and a communication cable.

Figure 4:
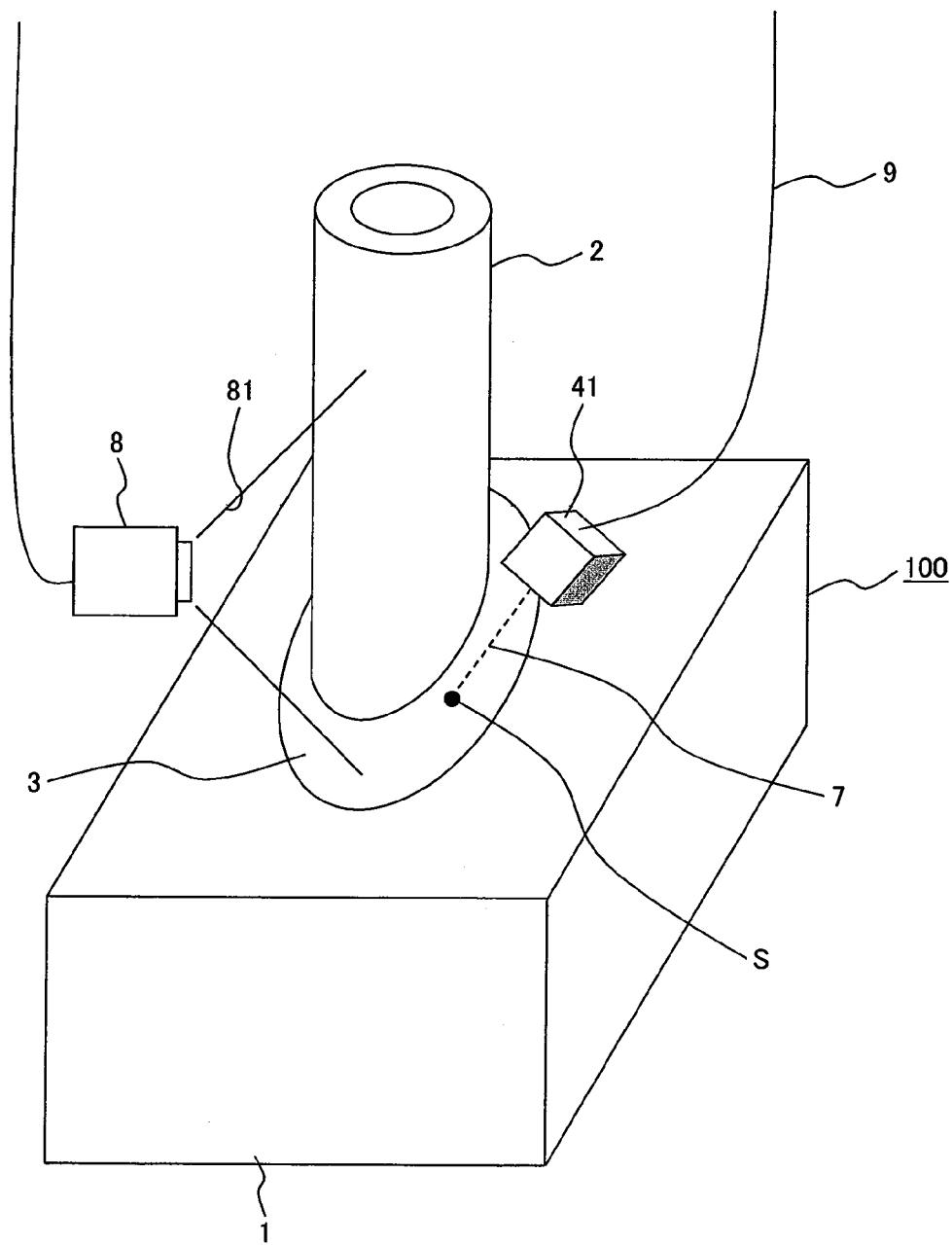
FIG. 4 is an illustrative diagram showing an ultrasonic inspection method in accordance with the embodiment 1.

FIG. 4 is an illustrative diagram of an ultrasonic inspection system that employs the ultrasonic sensor 41 in which the laser 6 is incorporated and is based on an immersion technique. When inspection is performed on the welded part 3 of the test object 100 using an ultrasonic wave emitted from the ultrasonic sensor 41, the visible laser beam 7 is irradiated from the ultrasonic sensor 41 at the same time. The visible laser beam is irradiated to an incident position of the ultrasonic wave. A laser beam irradiated position S of the visible laser beam 7 is imaged by a camera 8, so that a superficial state at the incident position of the ultrasonic wave can be checked.

Embodiment 2

Figure 5:
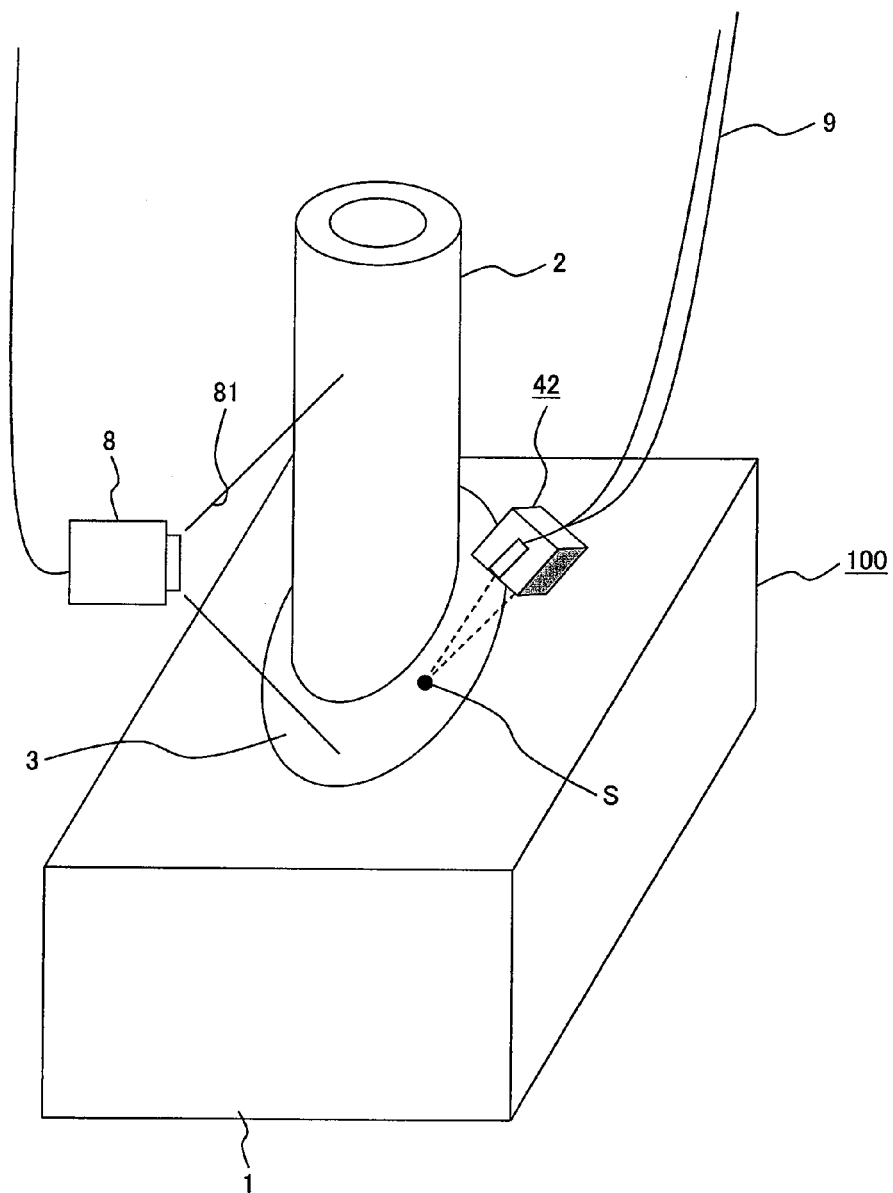
FIG. 5 is an illustrative diagram showing an ultrasonic inspection method in accordance with an embodiment 2.

FIG. 5 is an illustrative diagram showing an ultrasonic inspection system in accordance with an embodiment 2 that employs an ultrasonic sensor 42 on which lasers 6A and 6B are mounted. The same reference numerals are assigned to components identical to those of the embodiment 1. A visible laser beam 7A irradiated from the laser 6A and a visible laser beam 7B irradiated from the laser 6B have travelling directions thereof angled with respect to the ultrasonic wave emitting surface of the ultrasonic sensor 42 so that the laser beams can intersect at a predetermined position. In this state, by varying the distance between the ultrasonic sensor and test object, the irradiated positions S of the visible laser beams irradiated to the test object 100 are imaged by the camera 8. Eventually, the irradiated positions may coincide with each other as one point or separate from each other as two points.

Figure 6:
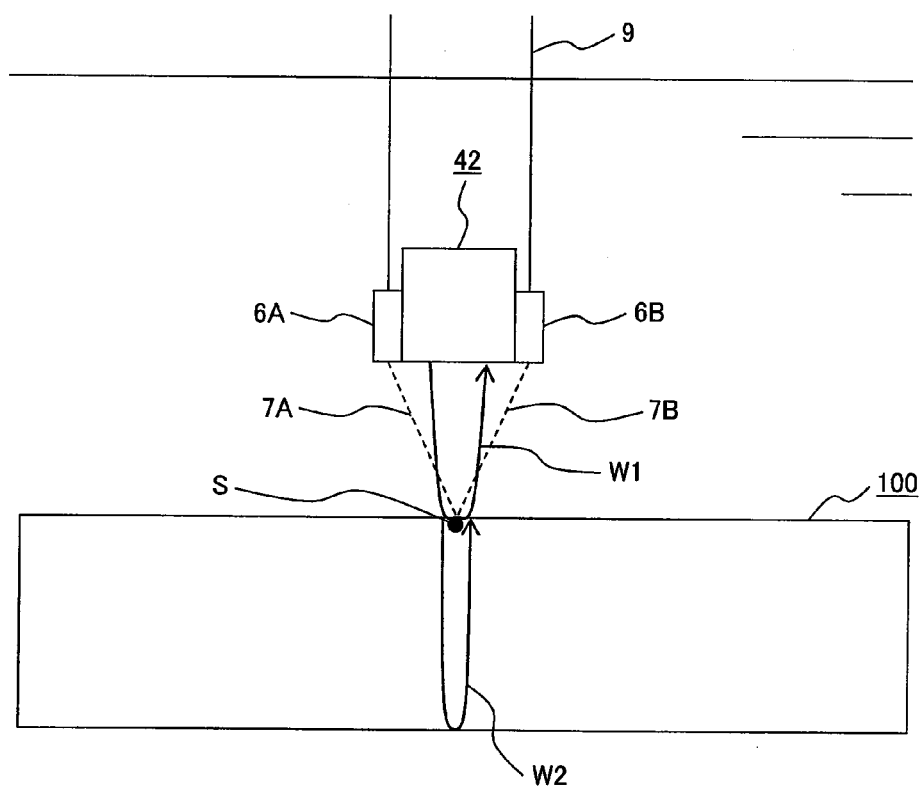
FIG. 6 is an illustrative diagram showing an ultrasonic sensor included in the embodiment 2 of the present invention.

FIG. 6 shows an ultrasonic sensor included in the ultrasonic inspection system in accordance with the embodiment 2. The ultrasonic sensor 42 is structured to have two lasers 6A and 6B mounted thereon in a width direction thereof. The optical axes of the lasers are tilted toward each other so that a visible laser beam 7A irradiated from the laser 6A and a visible laser beam 7B irradiated from the laser 6B can intersect at a position separated by a predetermined distance from the ultrasonic wave emitting surface of the ultrasonic sensor. An ultrasonic wave emitted from the ultrasonic sensor 42 incidents the test object 100 in the same manner as it does in the embodiment 1.

As shown in FIG. 6, when the irradiated positions S coincide with each other as one point, an incident position of an ultrasonic wave can be checked. When the point of intersection of the visible laser beams 7 shown in FIG. 6 is pre-set so that the distance to the point of intersection can be consistent with the water distance between the ultrasonic sensor and test object, the water distance that counts in the immersion technique can be monitored during a inspection movement.

Further, when the irradiated positions separate, as shown in FIG. 7, from each other as points S1 and S2, the width direction of the ultrasonic sensor 42 coincides with the direction of a straight line linking the two points. Therefore, the orientation of the ultrasonic sensor 42 can be checked.

Embodiment 3

FIGS. 8A and 8B and FIGS. 9A and 9B show an embodiment 3 of the present invention. In the present embodiment, the ultrasonic sensor included in the embodiment 2 is realized with an array transducer composed of plural transducers. An ultrasonic sensor 43 included in the embodiment 3 includes a one-dimensional array transducer 50 having transducers arrayed one-dimensionally. Delay times of ultrasonic waves generated from the plural transducers of the one-dimensional array transducer 50 are controlled to achieve inspection. An array transducer having transducers arrayed in two-dimensionally provides the same advantage.

Figure 8A:
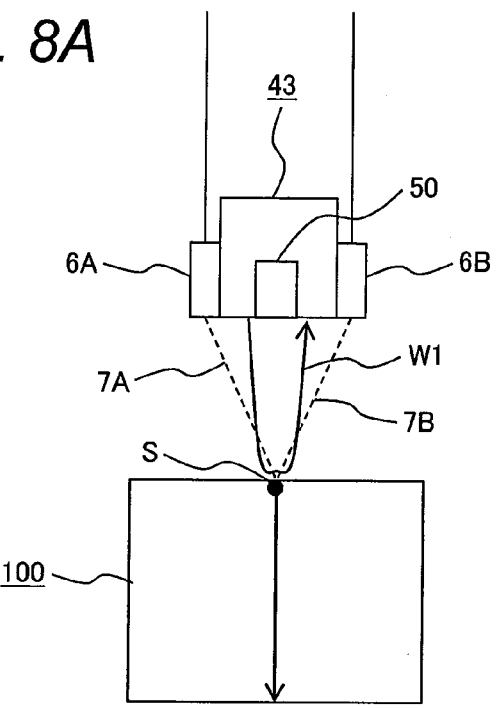
FIG. 8A is a front view showing a sectorial scan performed with an array transducer employed in an embodiment 3.
Figure 8B:
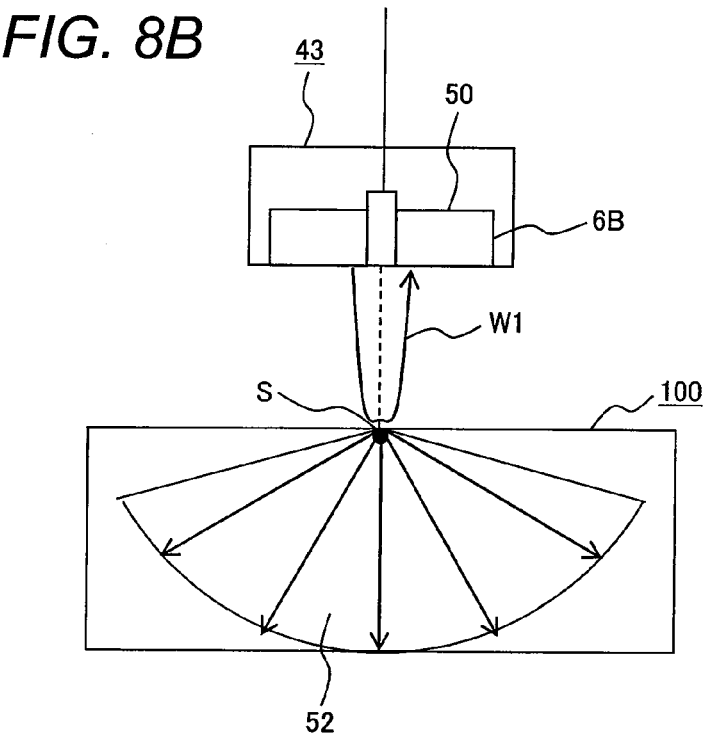
FIG. 8B is a side view showing the sectorial scan performed with the array transducer employed in the embodiment 3.
Figure 9A:
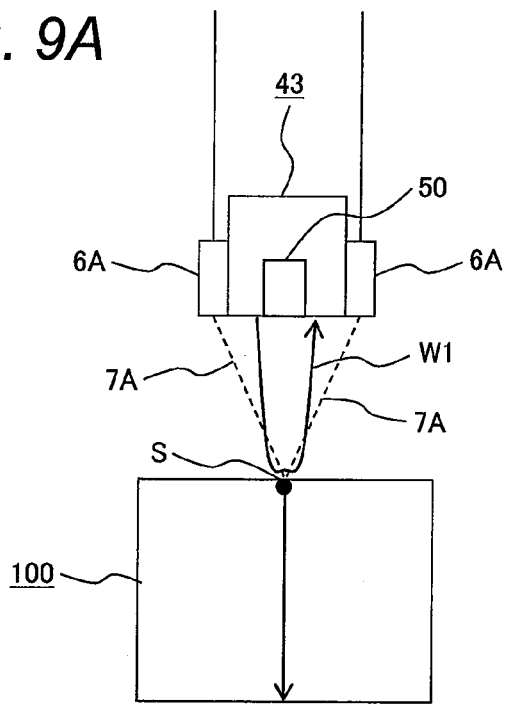
FIG. 9A is a front view showing a linear scan performed with the array transducer employed in the embodiment 3.
Figure 9B:
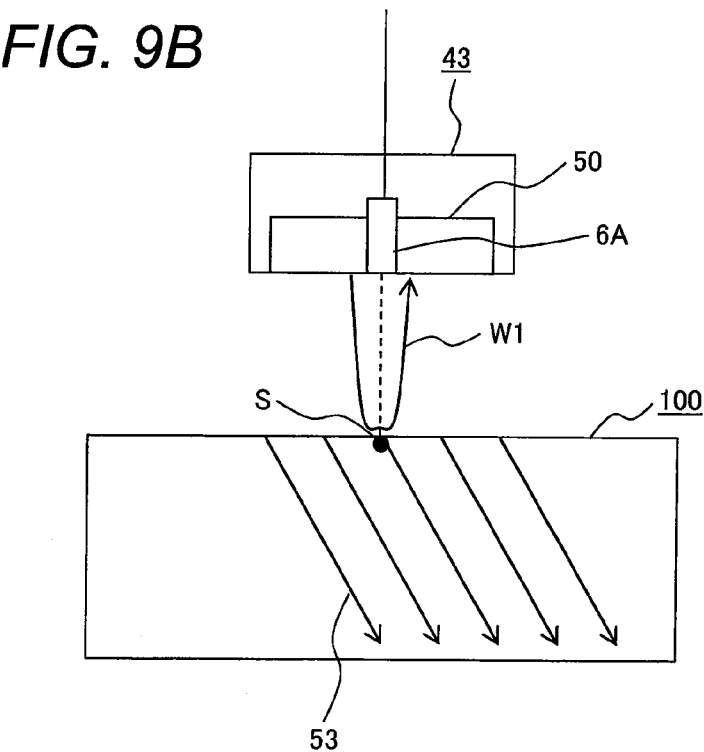
FIG. 9B is a side view showing the linear scan performed with the array transducer employed in the embodiment 3.

Owing to adoption of the array transducer, ultrasonic waves can be, as shown in FIGS. 8A and 8B, caused to simultaneously incident an test object at various angles. Therefore, a sector scanning plane 52 can be scanned. In addition, as shown in FIGS. 9A and 9B, ultrasonic waves can be caused to linearly incident over a wide range in order to scan a linear scanning plane 53. Therefore, a load on an access mechanism can be lightened. In addition, a result of ultrasonic inspection performed on a section of the test object can be instantaneously imaged. The present embodiment is therefore quite useful in quickly conducting an inspection.

Embodiment 4

Figure 10:
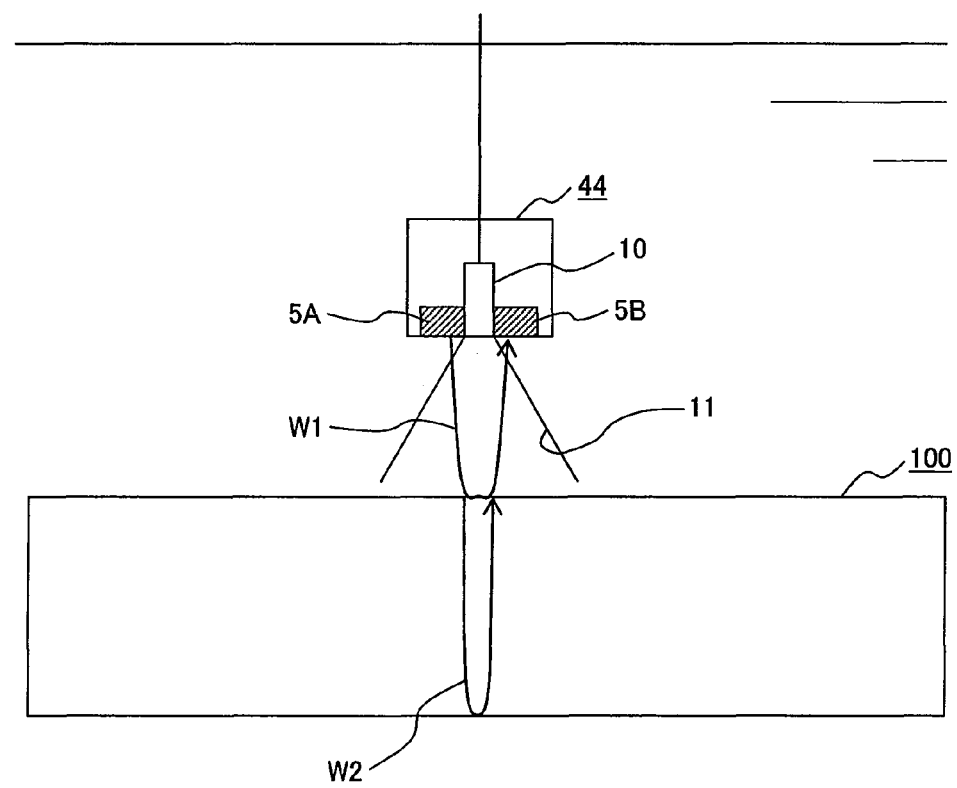
FIG. 10 is an illustrative view showing an ultrasonic sensor included in an embodiment 4 of the present invention.
Figure 11:
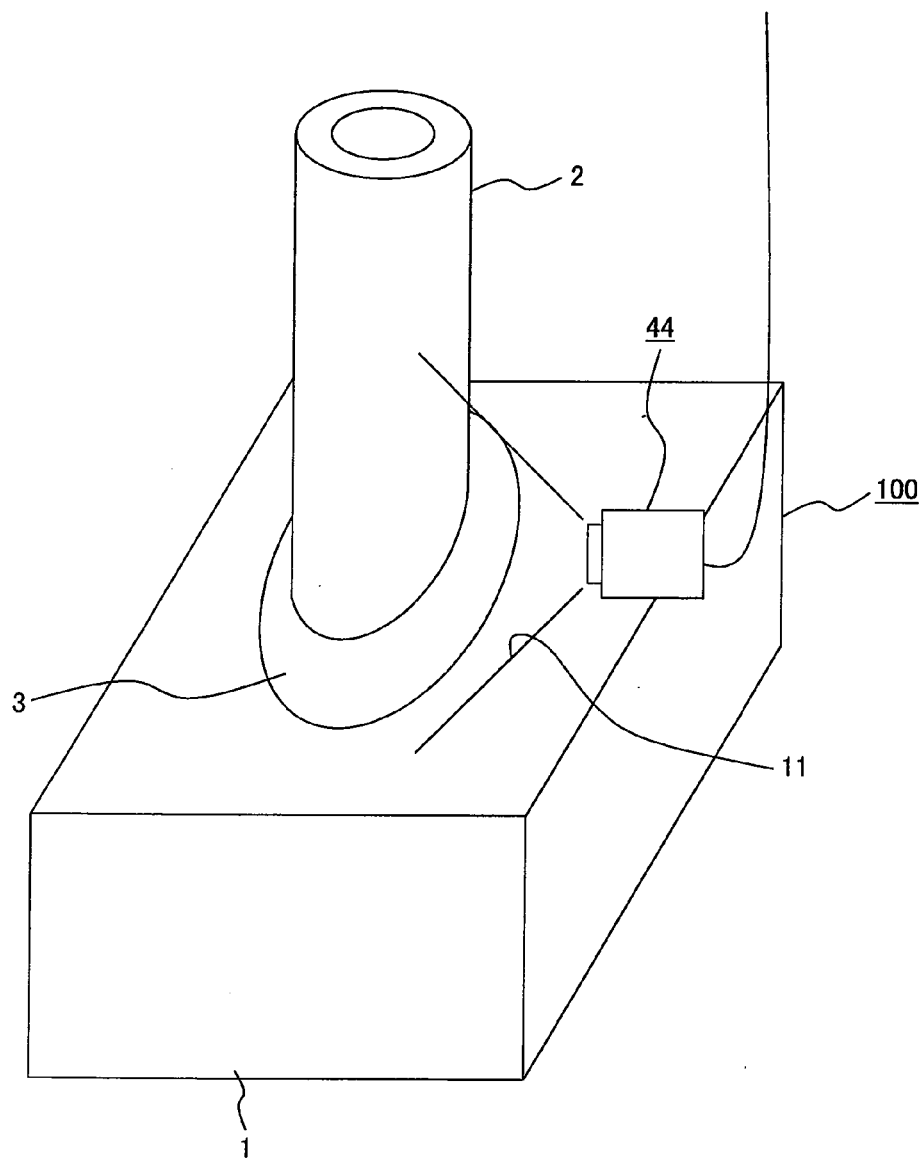
FIG. 11 is an illustrative view showing an ultrasonic inspection method in accordance with the embodiment 4.
Figure 12:
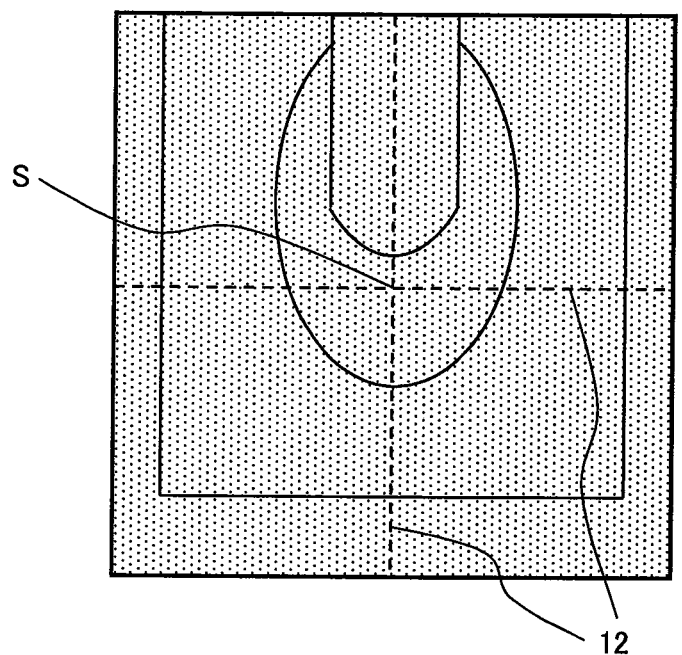
FIG. 12 is an illustrative view showing an example of an image picked up by a fiberscope included in the embodiment 4; [E]

FIG. 10 shows an embodiment 4 of the present invention. An ultrasonic sensor 44 included in the embodiment 4 is structured to have a fiberscope 10 incorporated therein. The fiberscope 10 has an illumination light source and a camera mounted in the distal part thereof. FIG. 11 is a diagram illustratively showing an ultrasonic inspection method that is based on an immersion technique and employs the ultrasonic sensor 44 having the built-in fiberscope 10. FIG. 12 shows an example of an image picked up by the fiberscope. In FIG. 12, symbol S denotes an ultrasonic wave incident position, that is, a laser beam irradiated position, reference numeral 12 denotes center lines of an image picked up the fiberscope 10, and reference numeral 11 denotes a viewing angle of the fiberscope.

An ultrasonic wave emitted from the ultrasonic sensor 44 is used to detect a flow in a welded part of an test object, and an ultrasonic wave incident position can be imaged by the fiberscope 10 at the same time. Therefore, a inspection system including an imaging system can be constructed compactly.

[F]

Figure 13:
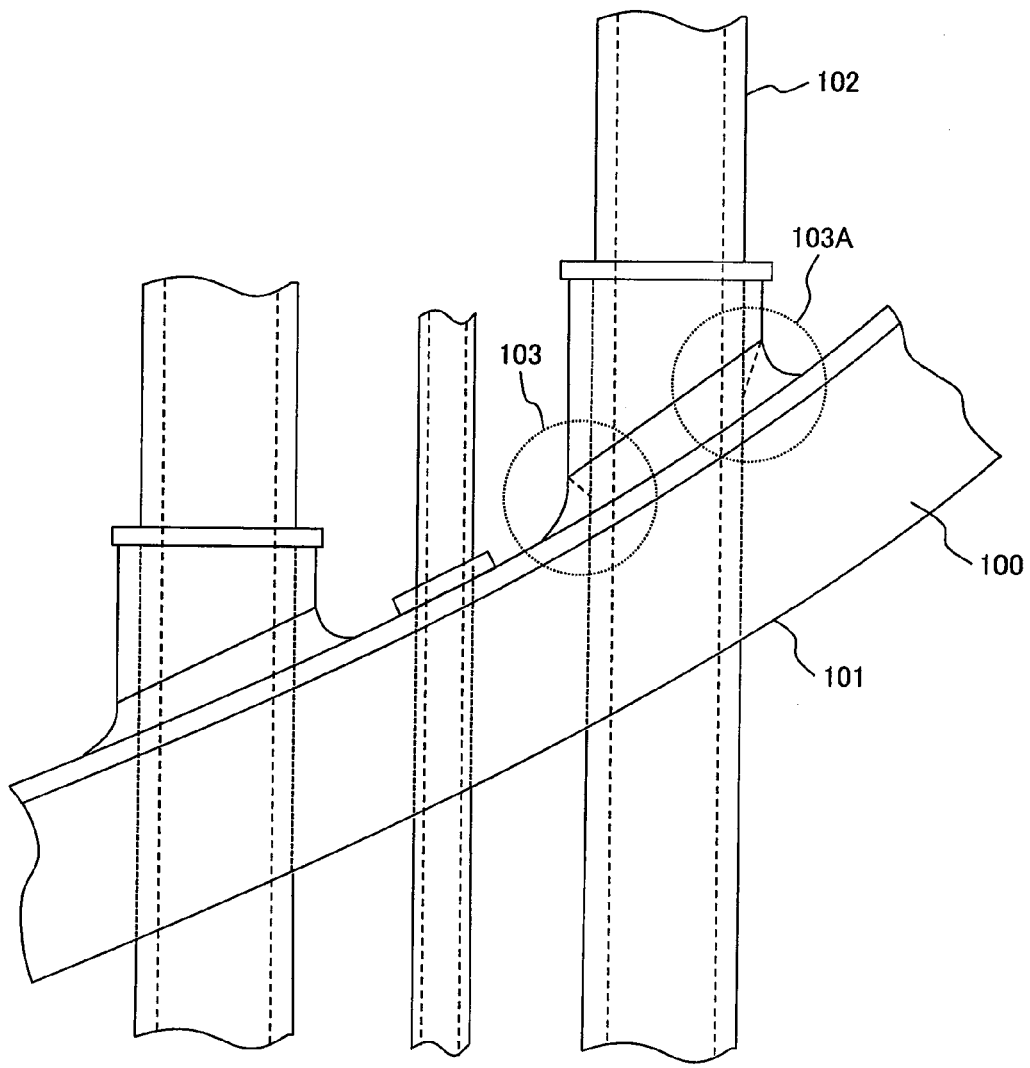
FIG. 13 is a sectional view of an test object to which the present invention is adapted.

FIG. 13 is a sectional view of an test object 100 that has a pipe 102 penetrated through a steel plate 101 at a predetermined angle and that is an object to which the present invention is adapted. The periphery of the pipe 102 is welded to form a welded part 103. Water is adopted as a medium that propagates an ultrasonic wave. The presence or absence of a flaw in the welded part 103 is inspected through ultrasonic inspection based on an immersion technique. The shape of the welded part 103 three-dimensionally varies depending on an angle in a circumferential direction of the pipe 102. A welded part 103A on the soaring side of the steel plate is the narrowest, and has a shape making it difficult to accurately route an ultrasonic wave to an intended position.

Embodiment 5

(Basic Configuration of a Inspection System)

Figure 14:
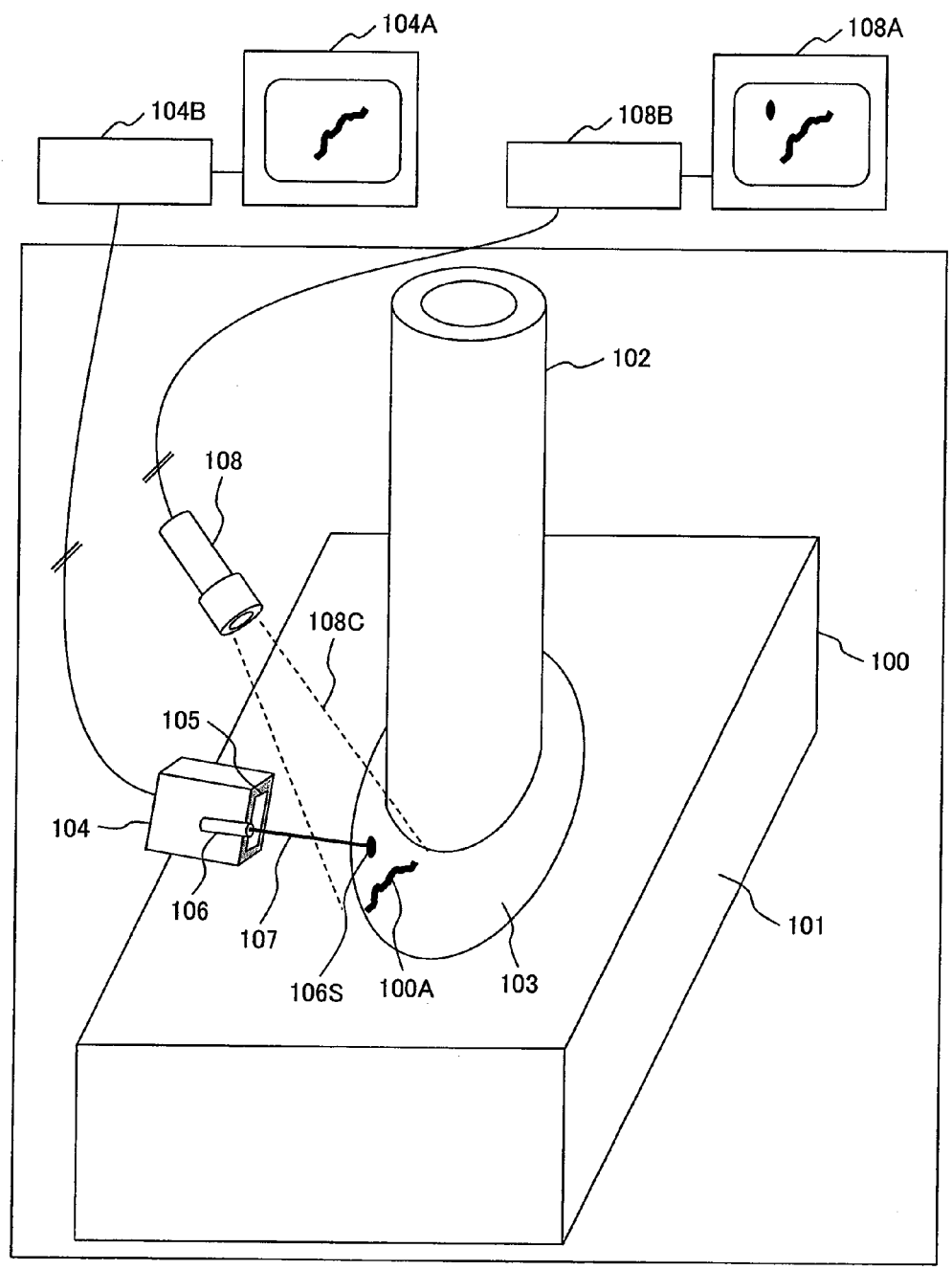
FIG. 14 is an illustrative diagram showing a configuration of an ultrasonic inspection system in accordance with an embodiment 5 of the present invention.

FIG. 14 shows a configuration of an ultrasonic inspection system employed in the embodiment 5 of the present invention. On an ultrasonic sensor 104 that is an ultrasonic wave transmitting/receiving unit, a laser marker 106 is mounted as an optical irradiator that irradiates an optical marker, that is, a specific optical pattern with which an arbitrary position on the surface of an test object is identified.

The ultrasonic sensor 104 is positioned above the inspecting surface of an test object 104 via a liquid (for example, water). In response to a driving signal fed from an ultrasonic wave transmitting/receiving device 104B, the ultrasonic sensor 104 generates an ultrasonic wave through an ultrasonic wave transmitting/receiving surface 105 thereof, propagates the ultrasonic wave toward the object 100, detects a reflected wave occurring on the surface of the test object 100 or in the interior of the test object, and inputs a receiving signal to the ultrasonic wave transmitting/receiving device 104B.

The laser marker 106 irradiates a laser beam to an ultrasonic wave incident position on the surface of the test object 100 of an ultrasonic wave emitted from the ultrasonic sensor 104. As the optical irradiator, aside from the laser marker, any unit capable of projecting an optical pattern, such as, a light bulb of visible light, an LED, or a liquid crystal projector will do.

An irradiated position 106S on the test object of an optical marker and the test object 100 are imaged using, for example, an underwater camera 108 as imaging equipment. Reference numeral 108C denotes a field of view of the camera. An area on the test object 100 which an ultrasonic wave incidents is imaged, or an area in which a reflected wave occurs is imaged.

The ultrasonic sensor 104 is connected to the ultrasonic wave transmitting/receiving device 104B. An ultrasonic image is displayed as information on a result of inspection on an acoustic image display device 104A. An image signal produced by the underwater camera 108 is fed to a camera controller 108B and displayed as a pickup image on an optical image display device 108A.

Figure 15:
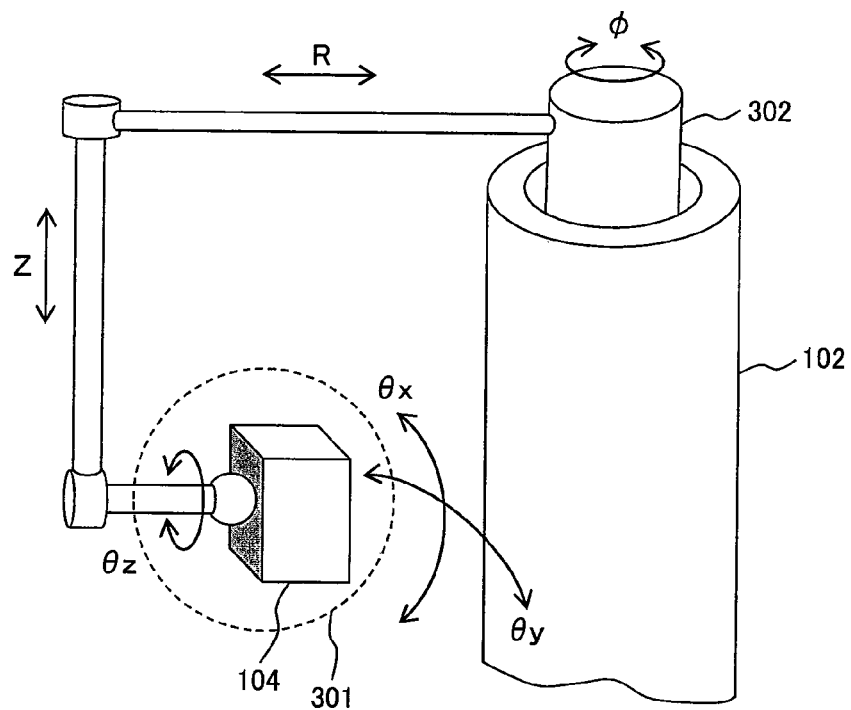
FIG. 15 is an illustrative diagram showing a moving mechanism for an ultrasonic sensor included in the embodiment 5 of the present invention.

FIG. 15 is an illustrative diagram for explaining a method of moving the ultrasonic sensor of the ultrasonic inspection system. In order to sweep the ultrasonic sensor 104, a manipulator that controls six or more axes and is adapted to a robot or the like is used, that is, a head 301 that has three rotating shafts θx, θy, and θz which rotate with the ultrasonic sensor 104 as a center and with axial directions X, Y, and Z as axes of rotation, is used in combination with an overall moving mechanism 302 that dwells in a pipe 102, and has three shafts which permit the entire head to move, that is, an up-and-down shaft (Z shaft), a radial-direction shaft (R shaft), and a rotating shaft (φ shaft).

The constitution of the embodiment 5 is applied to a nondestructive inspection intended to detect a defect in a welded part of an intra-reactor structure, such as, a stub tube of a control rod driving mechanism in a nuclear power plant, an intra-reactor instrumentation tube stand housing therein, a shroud support therein, or a shroud therein, or to measure the dimensions of the welded part. The method and system in accordance with the embodiment 5 can be applied to, in addition to a curved surface characteristic of the intra-reactor structure, a pipe or an object of inspection shaped like a flat plate.

Figure 16:
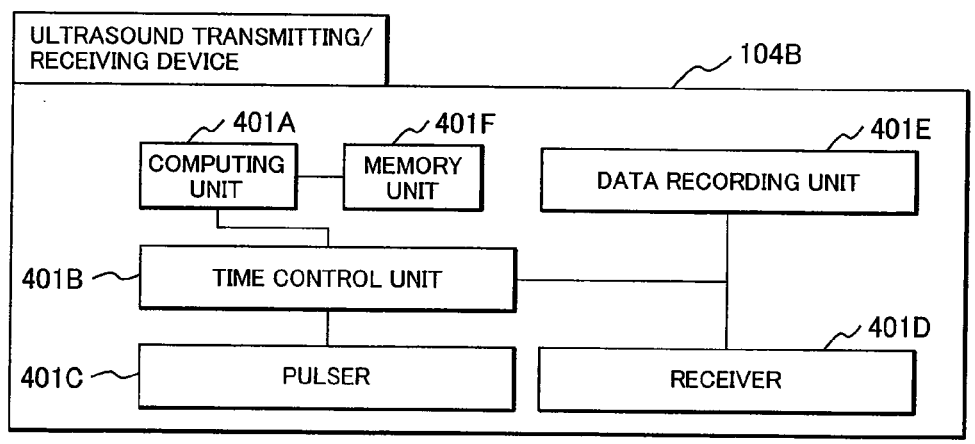
FIG. 16 is a diagram showing a configuration of an ultrasonic wave transmitting/receiving unit included in the embodiment 5 of the present invention.

As shown in FIG. 16, the ultrasonic wave transmitting/receiving device 104B includes a computing unit 401A, a time control unit 401B, a pulser 401C, a receiver 401D, and a data recording unit 401E. The pulser 401C feeds a driving signal to the ultrasonic sensor 104, and the receiver 401D processes a receiving signal inputted from the ultrasonic sensor 104.

The computing unit 401A controls the time control unit 401B, pulser 401C, receiver 401D, and data recording unit 401E so as to ensure necessary actions. Reference numeral 401F denotes a memory unit.

To begin with, the time control unit 401B controls the timing of a driving signal outputted from the pulser 401C, and also controls the timing at which the receiver 401D inputs a receiving signal. Therefore, the receiving signals sent from the receiver 401C are sequentially stored in the data recording unit 401E synchronously with respective transmission signals. The data recording unit 401E processes the receiving signal fed from the receiver 401D, and feeds the resultant signal to the acoustic image display device 104A. The action of the acoustic image display device 104A will be described later.

(Ultrasonic Sensor)

Figure 17:
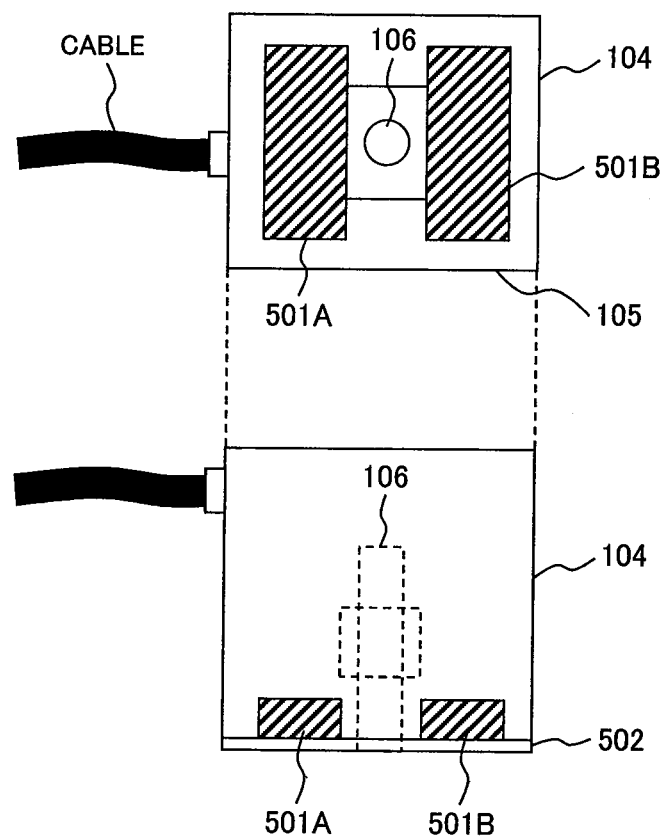
FIG. 17 is an illustrative diagram showing the ultrasonic sensor included in the embodiment 5 of the present invention.

Next, the ultrasonic sensor 104 will be detailed below. FIG. 17 is an illustrative diagram showing a basic construction of the ultrasonic sensor 104. An ultrasonic wave generation element is realized with a piezoelectric transduction element made of a piezoelectric ceramic or piezoelectric polymer. A front plate 502 is included for protection of the ultrasonic wave generation element and for acoustic matching necessitated because of multiple reflection, and is abutted against an external medium (water or the like) of the ultrasonic sensor 104 while serving as an ultrasonic wave transmitting/receiving surface 105. The ultrasonic sensor 104 shown in FIG. 18 includes an ultrasonic oscillation element 601.

The ultrasonic sensor 104 includes as an irradiator, which irradiates an optical marker, for example, a visible-light laser marker 106. The laser marker may be, as shown in FIG. 17, positioned in the center of the ultrasonic sensor 104. Alternatively, as shown in an applied example shown in FIG. 18, the laser marker may be positioned on the flank of the ultrasonic sensor 104.

Figure 18:
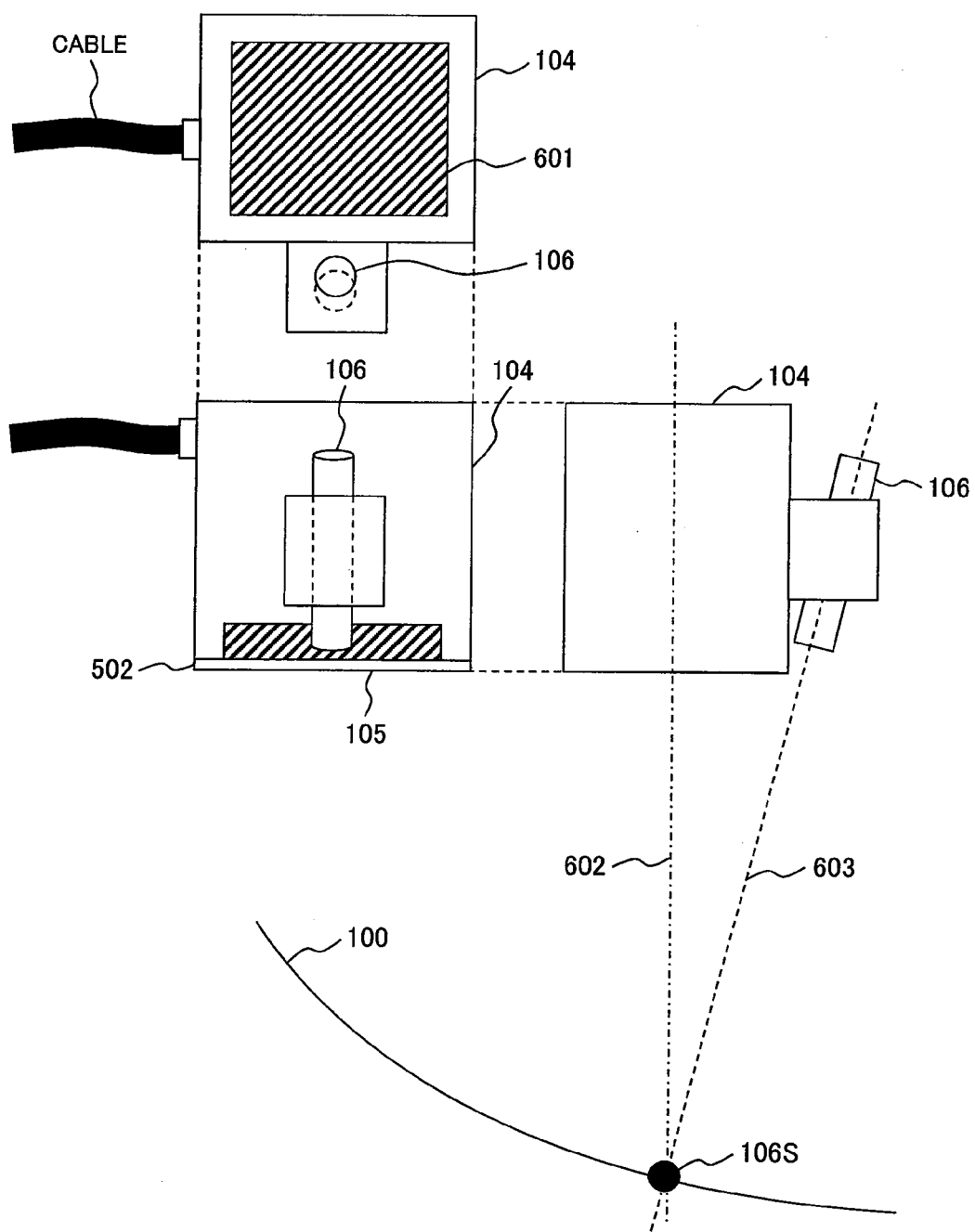
FIG. 18 is an illustrative diagram showing an example of an application of the ultrasonic sensor included in the embodiment 5 of the present invention.

As shown in FIG. 17, when the laser marker 106 is located in the center of the ultrasonic sensor 104, an ultrasonic wave generation element may be divided into two elements of a transmitting ultrasonic wave generation element 501A and a receiving ultrasonic wave generation element 501B. As shown in FIG. 18, when the laser marker 106 is placed on the flank of the ultrasonic sensor 104, the laser marker 106 may be tilted so that a sound axis 602 representing a propagating direction of an ultrasonic wave and an optical axis 603 representing a propagating direction of an optical marker can intersect at an irradiated position 106S of the marker on the test object 100.

(Ultrasonic Inspection Method)

Next, referring to FIGS. 19A and 19B, a description will be made of a ultrasonic inspection method in accordance with the present embodiment of the present invention and a display method for a result of inspection. Herein, a description will be made of a case where a defect on the surface of an test object is inspected using a surface wave (Rayleigh wave) deriving from a change of vibrational modes of an ultrasonic wave on the surface of the test object.

Figure 19A:
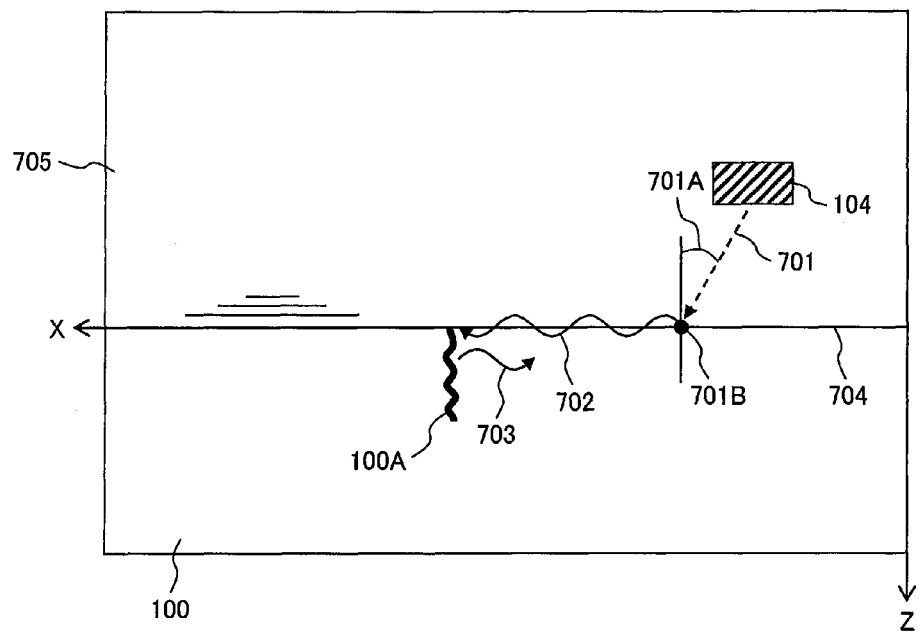
FIG. 19A is an explanatory diagram showing an acoustic image production method based on an ultrasonic wave and employed in the embodiment 5 of the present invention.

In FIG. 19A, an ultrasonic wave (oblique ultrasonic wave 701) is transmitted from the ultrasonic sensor 104 into a liquid 705 in an oblique direction. The oblique ultrasonic wave 701 reaches an incident position 701B on an interface 704 between the test object 100 and liquid 705, and has the vibrational mode thereof changed to the one in which a Rayleigh wave 702 occurs. At this time, an incident angle 701A at which the oblique ultrasonic wave 701 meets the interface 704 is provided as a critical angle θCR of a transverse wave according to an equation (1) below. For example, assuming that the liquid is water and the test object is a steel product, since an acoustic velocity of a longitudinal wave in water is 1480 m/s and an acoustic velocity of the transverse wave in the test object is 3200 m/s, θCR comes to approximately 27.5°. In reality, since an ultrasonic wave generated from a probe exhibits a spatial spread, as long as the incident angle is about 30°, the Rayleigh wave occurs in the test object with sufficient intensity.

$$\theta CR = \sin^{-1}(Cw/Cs) \quad (1)$$

where Cw denotes the acoustic velocity of a longitudinal wave in a liquid, and Cs denotes the acoustic velocity of a transverse wave in the test object.

The ultrasonic wave transformed into the Rayleigh wave on the interface 704 propagates on the surface of the test object. If a defect 100A serving as a reflection source exists in the surface or near the surface, the ultrasonic wave reflects from the defect, changes the travelling direction thereof, and propagates as the Rayleigh wave 703 on the surface of the test object. While the Rayleigh wave is propagating on the surface, part of the energy leaks out as an ultrasonic wave to the liquid and test object. The leaking ultrasonic wave is received by the ultrasonic sensor 104 again.

Figure 19B:
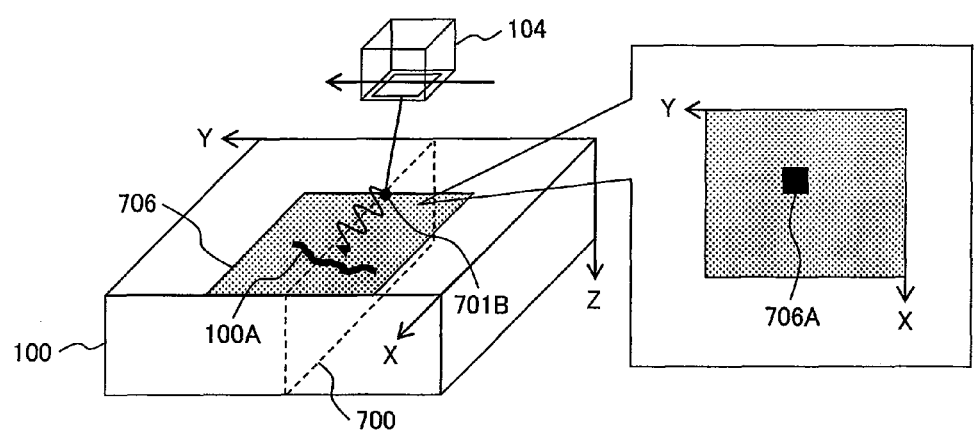
FIG. 19B is a perspective view showing the acoustic image production method based on an ultrasonic wave and employed in the embodiment 5 of the present invention.

FIG. 19B is a perspective view three-dimensionally expressing what is shown in FIG. 19A. In the drawing, a section 700 is equivalent to what is shown in FIG. 19A.

Figure 20:
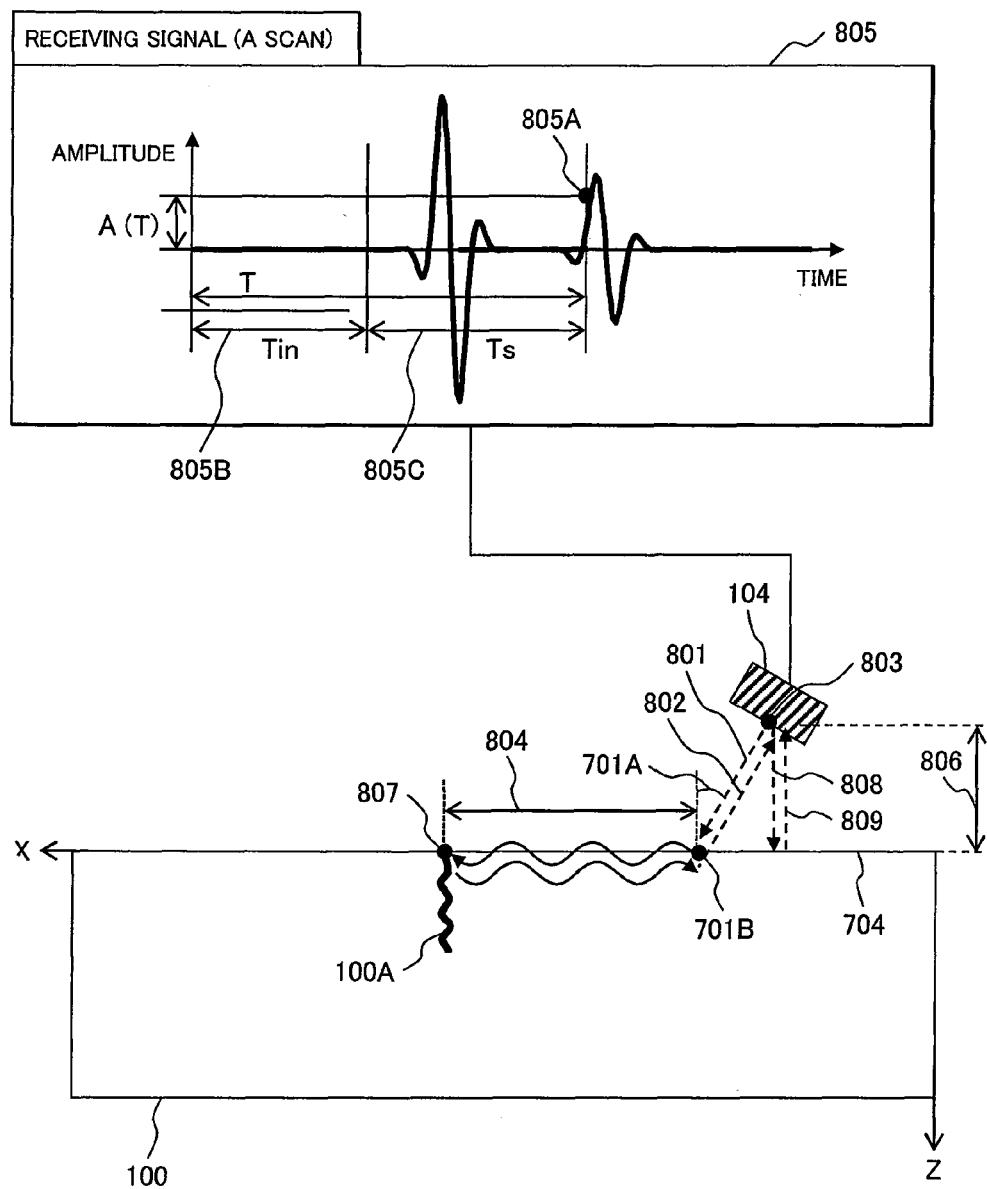
FIG. 20 is an explanatory diagram showing production of an acoustic image based on an ultrasonic wave and employed in the embodiment 5 of the present invention.

In FIG. 20, a receiving wave at the incident position 701B is recorded as an A scope signal 805 by indicating a time on the axis of abscissas and an amplitude on the axis of ordinates. In order to obtain the position of the defect 100A, the position of an ultrasonic wave transmitting point 803 is regarded as a reference, and a propagation distance 804 between the incident position 701B and the surface of the steel product is obtained.

Herein, the ultrasonic wave transmitting point 803 of the ultrasonic sensor 104 shall be already known. In an actual inspection, for example, owing to the moving mechanism included in the multiaxial manipulator, which is shown in FIG. 14, for moving the ultrasonic sensor 104 to a region to be inspected, the position of the ultrasonic sensor 104 can be identified with the origin in the moving mechanism as a reference.

However, as described in relation to an object of the present invention, the actual dimensions (as-built dimensions) of an actual object of inspection may not be fully consistent with dimensions instructed in a drawing (nominal dimensions), though it depends on a way of finishing a welded part through machining. In this case, it becomes hard to accurately grasp the positional relationship between the incident position 701B on the test object 100 and the transmitting point 803 on the basis of the nominal dimensions instructed in the drawing.

In the present invention, the incident position 701B (Xin, Yin,Zin) can be identified as the position of an optical marker irradiated to an test object according to a method to be described later.

In relation to the signal 805 received at the transmitting point 803, a reciprocating propagation time Tin in a liquid can be obtained according to an equation (2) below.

$$T\text{in} = D/Cw \quad (2)$$

where Cw denotes the acoustic velocity of a longitudinal wave in a liquid.

Herein, the distance D is a distance 806 between the ultrasonic sensor 104 and test object 100 (herein, a distance which an ultrasonic wave propagates in a liquid). According to the equation (2), the reciprocating propagation time Tin obtained from the receiving wave is known. Therefore, the water distance D is obtained as a product of Tin by Cw.

As an ultrasonic wave propagation route along which an ultrasonic wave is reflected from the surface of the test object 100, there are two routes, that is, a route along which the ultrasonic wave reciprocates by following paths 801 and 802, and a route along which the ultrasonic wave reciprocates by following paths 808 and 809. In the case of the route including the paths 808 and 809, since the ultrasonic wave nearly perpendicularly incidents the surface of the test object, the reflectance at the surface of the test object is high. Therefore, a receiving signal having propagated along the route including the paths 808 and 809 has a large magnitude and is temporally quickly received. Therefore, the equation (2) conditions the route including the paths 808 and 809.

When the incident position 701B on the test object 100 is regarded as a reference point in a system of coordinates, since the distance D is already known, X, Y, and Z coordinates (X0,Y0,X0) representing the transmitting point 803 can be identified.

More particularly, as described later, an optical image that shows the irradiated position of a laser beam from the laser marker makes it possible to verify that an ultrasonic wave is transmitted from or received at a point near the reflection source 100A. When the ultrasonic sensor 104 is aligned using the moving mechanism shown in FIG. 14 so that the signal 805 of a Rayleigh wave can be recognized, it is verified that the receiving signal derives from a defect. In addition, it is verified that the angle 802 between the test object and the propagating direction of the ultrasonic wave can be handled as being equal to the angle θCR at which the Rayleigh wave occurs.

As mentioned above, since the distance D between the test object and ultrasonic wave propagating direction and the angle θ 802 can be identified, the X, Y, and Z coordinates (X0,Y0,Z0) representing the transmitting point 803 can be calculated. If the coordinates (Xin,Yin,Zin) representing the incident position 701B are already known, (X0,Y0,Z0) can be given by equations (3) below on the basis of the incident angle θ 701A with respect to the surface of the test object and the water distance D806.

$$X0 = X\text{in} - D \times \tan \theta CR$$

$$Y0 = Y\text{in}$$

$$Z0 = Z\text{in} - D \quad (3)$$

Out of the propagation time T, the reciprocating propagation time Tin in a liquid and the reciprocating propagation time Ts on the surface of the test object are given by an equation (4) below.

$$Ts = T - T\text{in} \quad (4)$$

Since the propagation time Ts on the surface of the test object is obtained, the X, Y, and Z coordinates (Xd,Yd,Zd) representing the position of a defect are calculated according to equations (5) below.

$$Xd(T) = Ts \times Cr/2 = (T - T\text{in}) \times Cr/2$$

$$Yd = Y0$$

$$Zd = 0 \quad (5)$$

where Cr denotes the acoustic velocity of a Rayleigh wave in the test object.

According to the equation (5), the X coordinate is a function of the propagation time T. An amplitude 805A attained when the propagation time T has elapsed is an amplitude A(T), a pixel value representing a shade or color whose level is associated with the amplitude (AT) is assigned to the X coordinate Xd. By moving the ultrasonic sensor 104 in the Y direction, an acoustic image on a two-dimension XY can be obtained.

(Method of Displaying a Result of Inspection)

Figure 21:
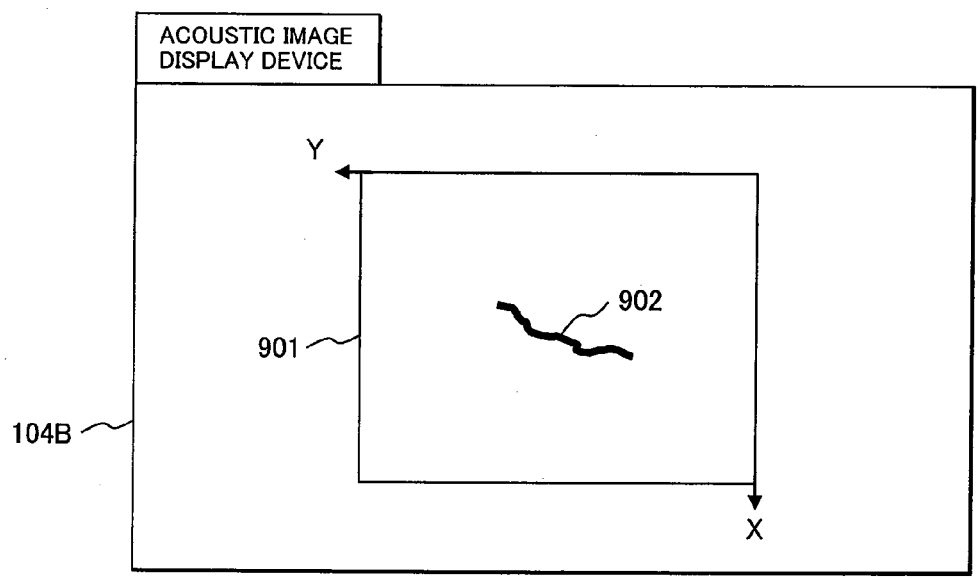
FIG. 21 is an illustrative diagram showing an acoustic image produced in the embodiment 5 of the present invention.

When a two-dimensional imaging range is rendered, it looks like an area 706 in FIG. 19B and is an area which an oblique ultrasonic wave incidents to be transformed into a Rayleigh wave. To a pixel 706A in the image area, for example, a value representing a shade or color whose level is associated with the amplitude A(T) is assigned as a pixel value (for example, when the amplitude is large, a value representing black is assigned; or when the amplitude is approximately 0, a value representing white is assigned). When the ultrasonic inspection system in accordance with the embodiment 5 is used to perform inspection near the defect 100A, an image like, for example, an image 901 in FIG. 21 is obtained. A defect image 902 having the similar shape as the defect 100A does can be obtained. Thus, the position, dimensions, and shape of the defect on the surface of an test object can be assessed.

Figure 22:
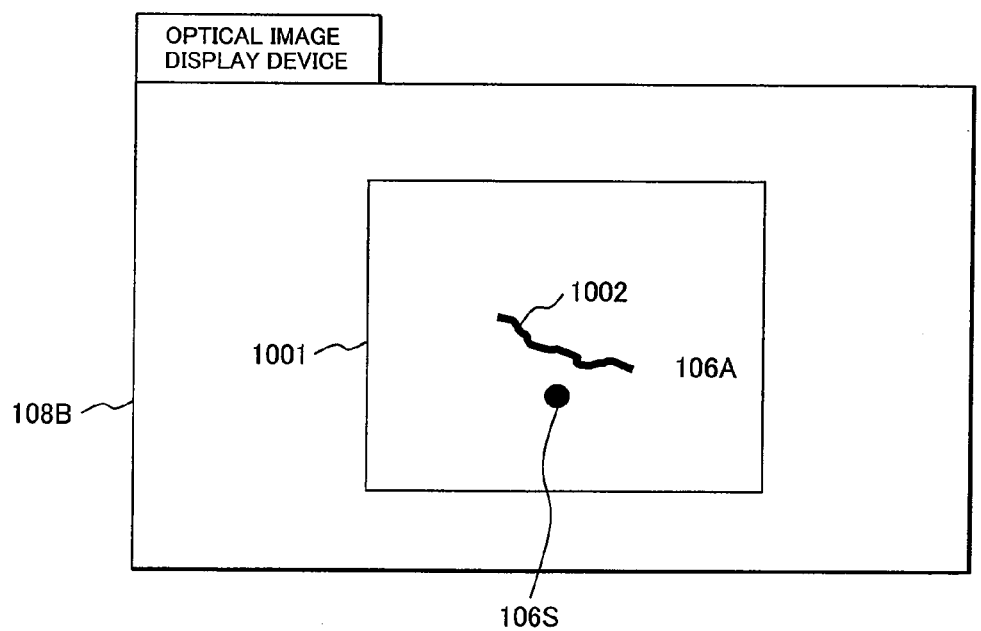
FIG. 22 is an illustrative diagram showing an optical image produced in the embodiment 5 of the present invention.

Now, an optical image showing an irradiated position of a laser beam from the laser marker will be described below. FIG. 22 shows an example of an optical image of the test object 100 picked up by the underwater camera 108 that is imaging equipment. The welded part 103 of the test object 100 has a flaw thereof detected with an ultrasonic wave transmitted from the ultrasonic sensor 104. At the same time, a visible laser beam 107 is irradiated from the ultrasonic sensor 104, and the incident position of the ultrasonic wave is visualized as an irradiated position 106S. The irradiated position 106S of the visible laser beam 107 is imaged by the underwater camera 108, whereby an optical image is displayed on the optical image display device 108A. Eventually, the incident position of the ultrasonic wave can be checked.

In an optical image 1001, when a reflection source such as the defect 100A is present on the surface of the test object, an optical pickup image 1002 of the defect is displayed in addition to the irradiated position 106S corresponding to the incident position of the ultrasonic wave.

In relation to the embodiment 5, a description has been made of an example of an ultrasonic sensor that adopts a piezoelectric transduction element as an ultrasonic wave transmitting/receiving unit and has transmitting and receiving abilities integrated into the ultrasonic wave transmitting/receiving unit. Alternatively, an ultrasonic wave transmitter and an ultrasonic wave receiver may be incorporated in the ultrasonic sensor.

A transmitting method in which an electromagnetic acoustic wave that gives electromagnetic force to a superficial part of an test object is employed, or a transmitting method in which a laser beam is irradiated to the surface of the test object so that an ultrasonic wave occurs due to a physical impact on the superficial part of the test object may be adopted as an ultrasonic wave transmitting method. In this case, in addition to a transmitted position of an ultrasonic wave, an occurring position of an ultrasonic wave to be received has to be identified. When the laser marker described in relation to the embodiment 5 is oriented in a propagating direction of the receiving ultrasonic wave, the ultrasonic wave occurring position can be identified in the same manner.

As mentioned above, according to the embodiment 5, an ultrasonic sensor including a laser marker is used to perform inspection, and an underwater camera is used to image an irradiated position of a laser beam from the laser marker. An acoustic image represented by an ultrasonic wave, and an optical image picked up by the underwater camera are displayed, whereby an incident position can be checked. In addition, by checking the incident position of an ultrasonic wave, the positional relationship (angle or distance) between an test object and the ultrasonic sensor can be readily recognized. Based on the acoustic image represented by the ultrasonic wave, the position of a defect on the surface of the test object, the dimensions thereof, or the shape thereof can be assessed. A highly reliable result of inspection can be provided.

Embodiment 6

Figure 23:
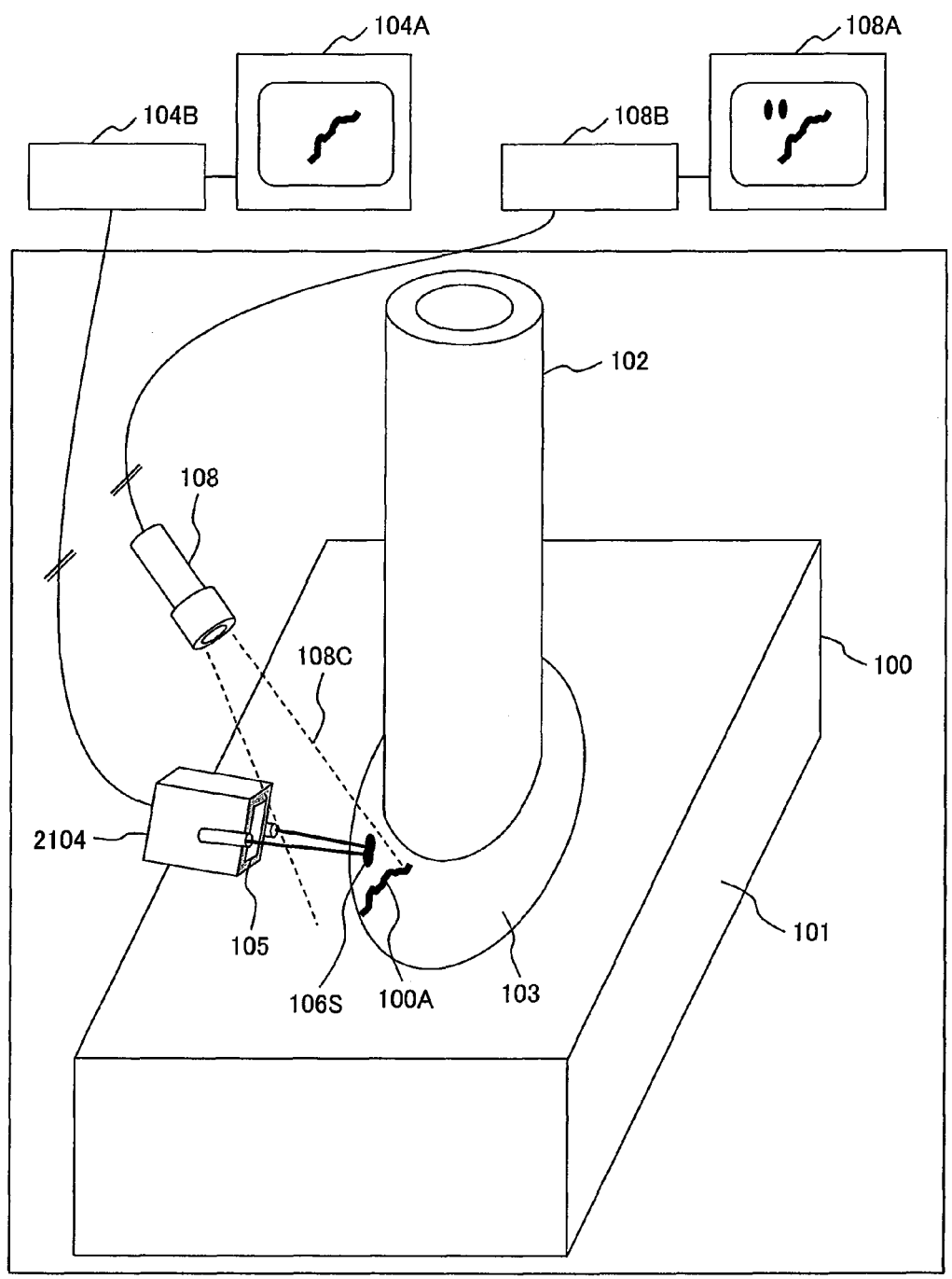
FIG. 23 is an illustrative diagram showing a configuration of an ultrasonic inspection system in accordance with an embodiment 6 of the present invention.

FIG. 23 shows a configuration of an ultrasonic inspection system employed in an embodiment 6. In the embodiment 6, plural optical irradiators are mounted on the ultrasonic sensor 104.

Figure 24:
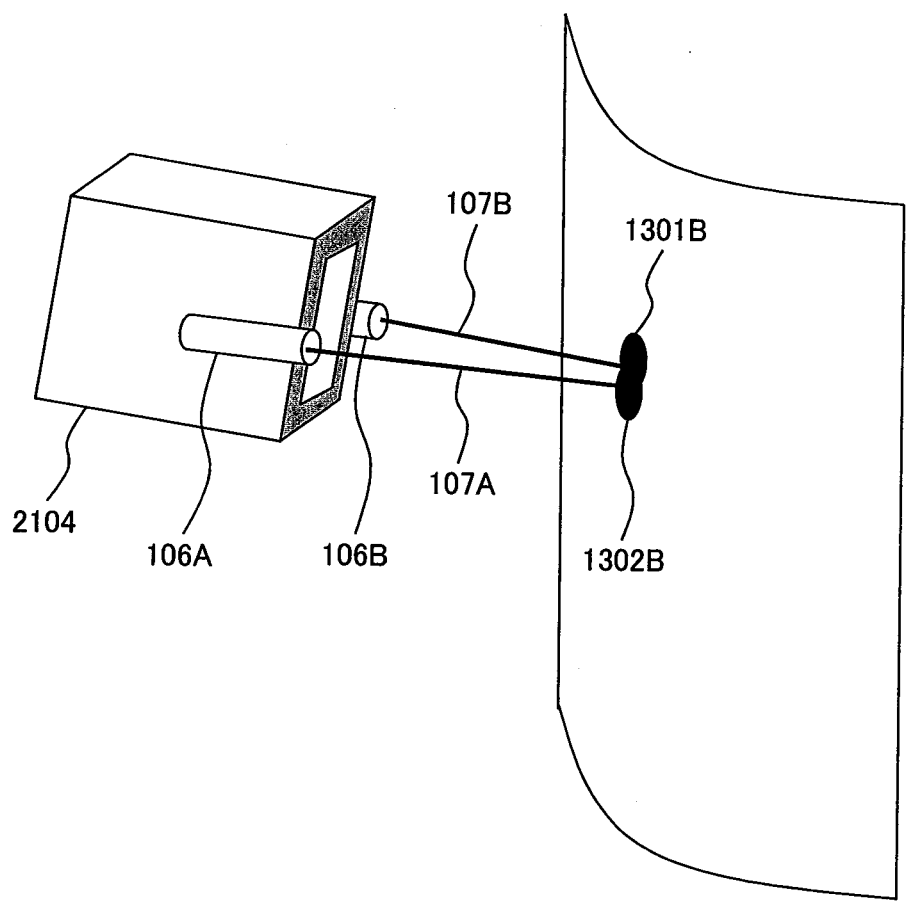
FIG. 24 is an illustrative diagram showing an ultrasonic sensor included in the embodiment 6 of the present invention.
Figure 25:
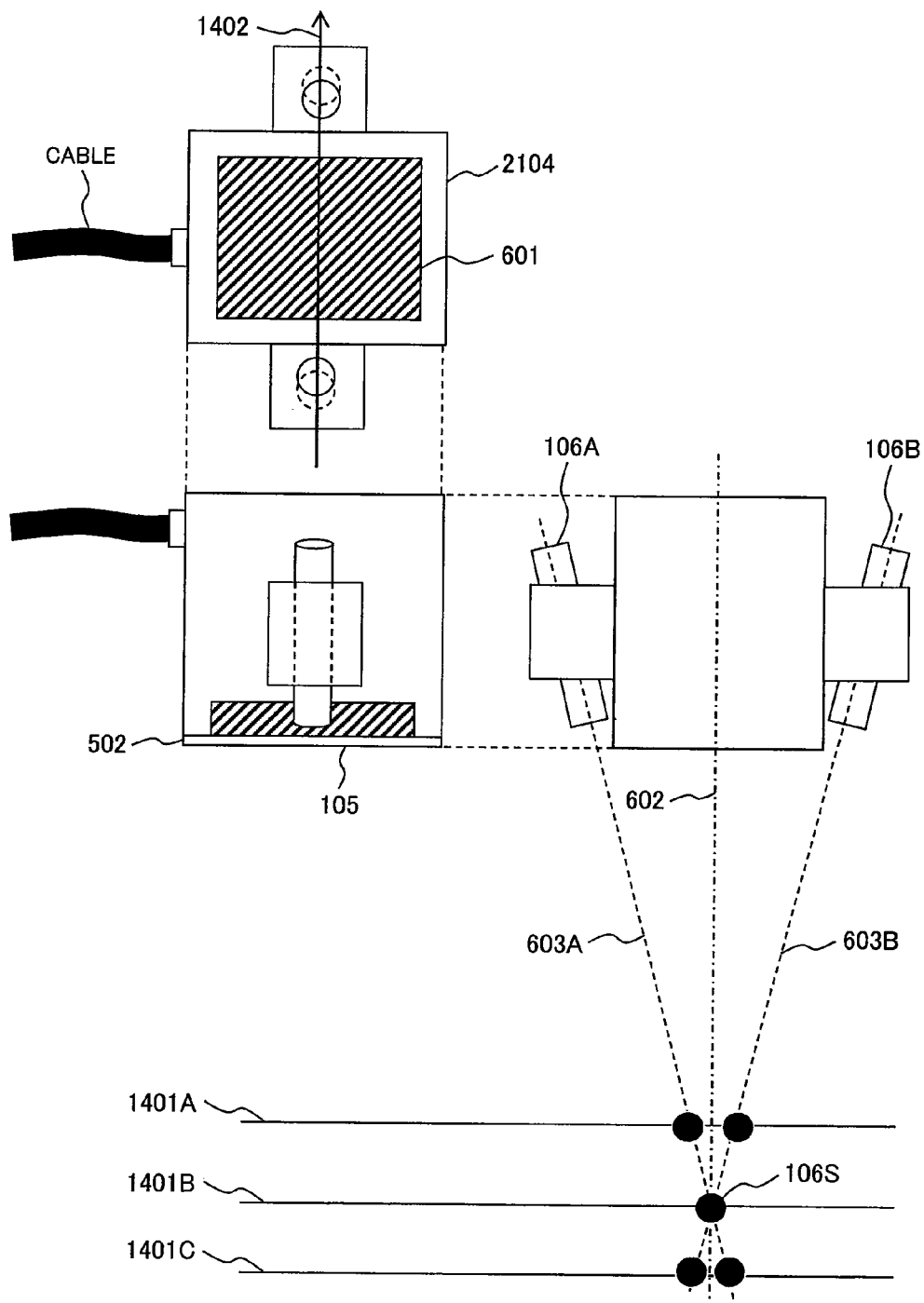
FIG. 25 is an illustrative diagram showing a distance measurement method that uses the ultrasonic sensor and is implemented in the embodiment 6 of the present invention.
Figure 26:
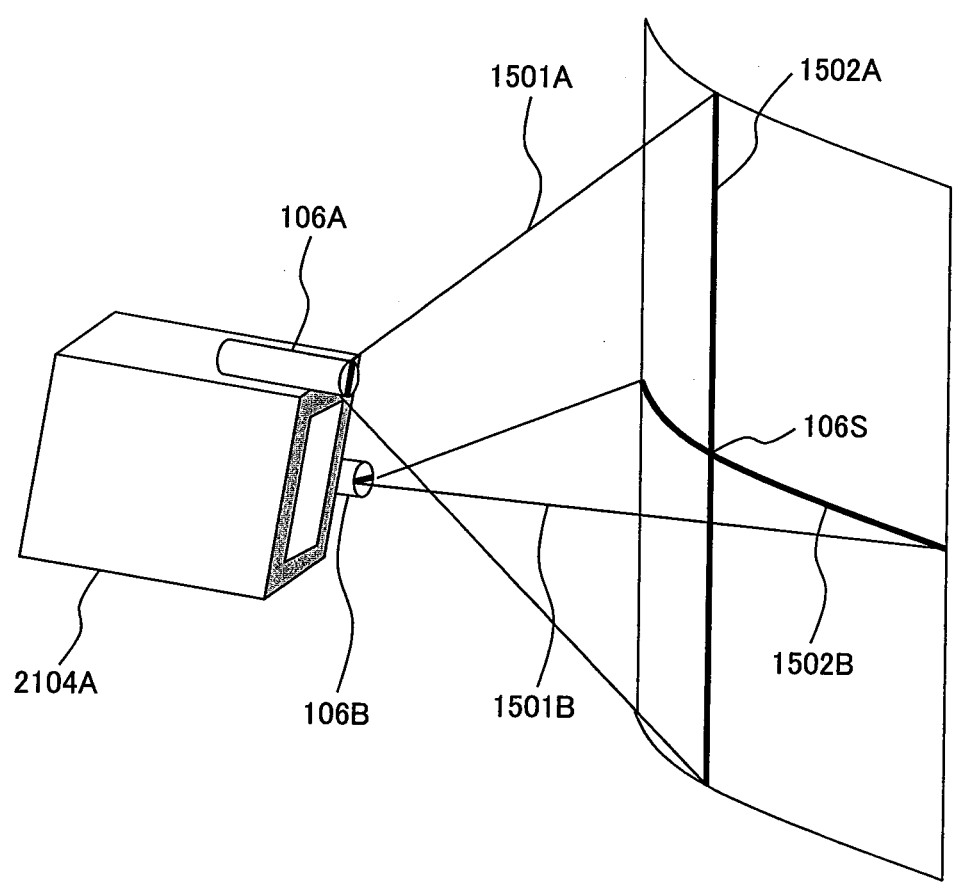
FIG. 26 is an illustrative diagram showing an example of an application of the ultrasonic sensor included in the embodiment 6 of the present invention.

A description will be made on the assumption that a laser marker is, similarly to the one in the embodiment 5, adopted as the optical irradiator. FIG. 24 to FIG. 26 are enlarged views of laser markers 106A and 106B included in the embodiment 6. FIG. 24 is concerned with a case where the shape of an optical marker on the surface of an test object is a spot and FIG. 25 shows a detailed arrangement. FIG. 26 is an illustrative diagram of a projection pattern obtained in a case where the shape of the optical marker on the surface of the test object is a line.

As shown in FIG. 25, the laser markers 106A and 106B are mounted on an ultrasonic sensor 2104 with the optical axes 603A and 603B thereof tilted toward each other so that beams irradiated from the laser markers 106A and 106B respectively can intersect at a predetermined irradiated position 106S that is separated by a predetermined distance from the ultrasonic wave emitting surface 105 of the ultrasonic sensor 104. The irradiated position 106S that is a point of intersection shall be located on a center sound axis 602 in an ultrasonic wave propagating direction.

As shown in FIG. 25, when the distance between the ultrasonic sensor 2104 and an test object is a predetermined distance 1401B, the position at which the beams irradiated from the laser markers intersect is one point. When the ultrasonic sensor gets closer to the test object (a position 1401A) or gets farther from the test object (a position 1401C), the beams irradiated from the laser markers meet the test object at two points.

The situation is monitored using the underwater camera 108 that is imaging equipment. By looking at an image displayed on the optical image display device 108A, it can be verified whether the irradiated positions 106S on the test object 100 of the beams from the laser markers coincide with each other to become one point or separate from each other to become two points.

When the irradiated positions 106S coincide with each other to become one point, the incident position of an ultrasonic wave and a distance can be identified. When the irradiated positions 106S of the beams from the laser markers separate from each other to become two points, it is seen that the ultrasonic sensor 104 and test object 100 are not separated from each other by a predetermined distance. The position of the point of intersection of the beams 107 is pre-set so that the distance to the position can be consistent with a predetermined water distance (for example, 30 mm) between the ultrasonic sensor and test object which counts in an immersion technique, whereby the water distance that counts in the immersion technique and varies during a inspection movement can be monitored. When the ultrasonic sensor 104 is swept using the moving mechanism, which is shown in FIG. 15, so that the irradiated positions of the beams from the laser markers can coincide with each other to become one point, the water distance can be set to a predetermined value. Thus, when two or more laser markers that irradiate beams that exhibit a spot-like shape on the surface of an test object are mounted, the distance between the test object 100 and ultrasonic sensor 104 can be identified based on optical images provided by the laser markers.

Further, when the laser markers are mounted on the opposite flanks of the ultrasonic sensor 104, if the irradiated positions of laser beams are two points, the direction of a straight line linking the two irradiated positions, and a direction 1402 linking the flanks of the ultrasonic sensor 104 on which the laser markers are disposed are consistent with each other. Therefore, the orientation (posture) of the ultrasonic sensor 104 can be identified.

As shown in FIG. 26, laser markers that irradiate beams exhibiting a line-like shape on the surface of an test object are used and mounted on the flank of an ultrasonic sensor 2104A and the top thereof respectively so that the beams irradiated from the laser markers can intersect each other. In this construction, an irradiated position 106S corresponding to an incident position of an ultrasonic wave can be identified based on a point of intersection between a line 1502A drawn with a linear beam 1501A irradiated from the laser marker 106A and a line 1502B drawn with a linear beam 1501B irradiated from the laser marker 106B. In addition, based on the directions of the lines 1502A and 1502B, the orientation of the ultrasonic sensor 104 can be identified irrespective of the distance between the test object 100 and ultrasonic sensor 104.

When the laser markers that irradiate beams exhibiting a line-like shape on the surface of an test object are employed, the distance between the test object 100 and ultrasonic sensor 104 can be obtained based on the propagation time of an ultrasonic wave as described in relation to the embodiment 5.

Figure 27:
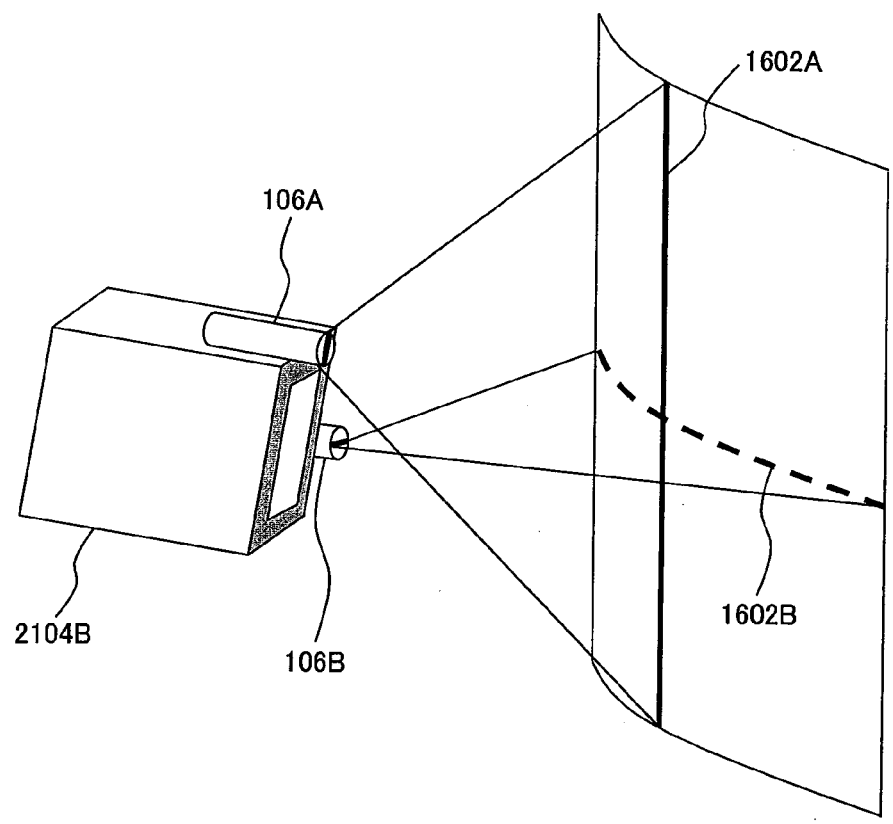
FIG. 27 is an illustrative diagram showing another example of an application of the ultrasonic sensor included in the embodiment 6 of the present invention.

As shown in FIG. 27, if the irradiation patterns for the beams which are irradiated from the laser markers and which exhibit a line-like shape on the surface of an test object are set to mutually different ones, when the orientation of the ultrasonic sensor is determined, from which of the laser markers 106A and 106B the projected line 1602A or 1602B derives can be readily recognized. This provides an effect of preventing a human error. As the irradiation patterns, for example, irradiation patterns that are different from each other in terms of a feature, that is, a color or a lighting time may be produced by employing, for example, a red laser and a green laser or a laser that is lit all the time and a laser that flickers.

As mentioned above, according to the embodiment 6, an ultrasonic sensor including two or more laser markers is used to perform inspection, and an underwater camera is used to image irradiated positions of beams from the laser markers. An acoustic image represented by an ultrasonic wave and an optical image picked up by the underwater camera are displayed, whereby the incident position of the ultrasonic wave can be checked. In addition, when the laser markers irradiate beams that exhibit a spot-like shape on the surface of an test object, the distance of the ultrasonic sensor from the test object and the orientation thereof can be identified. When the laser markers irradiate beams that exhibit a line-like shape on the surface of the test object, the orientation of the ultrasonic sensor with respect to the test object can be identified.

As mentioned above, in the embodiment 6, by checking the incident position of an ultrasonic wave, the positional relationship (angle or distance) between an test object and an ultrasonic sensor can be readily accurately identified. Based on an acoustic image represented by the ultrasonic wave, the position of a defect on the surface of the test object, the dimensions thereof, or the shape thereof can be assessed. A more highly reliable result of inspection can be provided.

Embodiment 7

Figure 28:
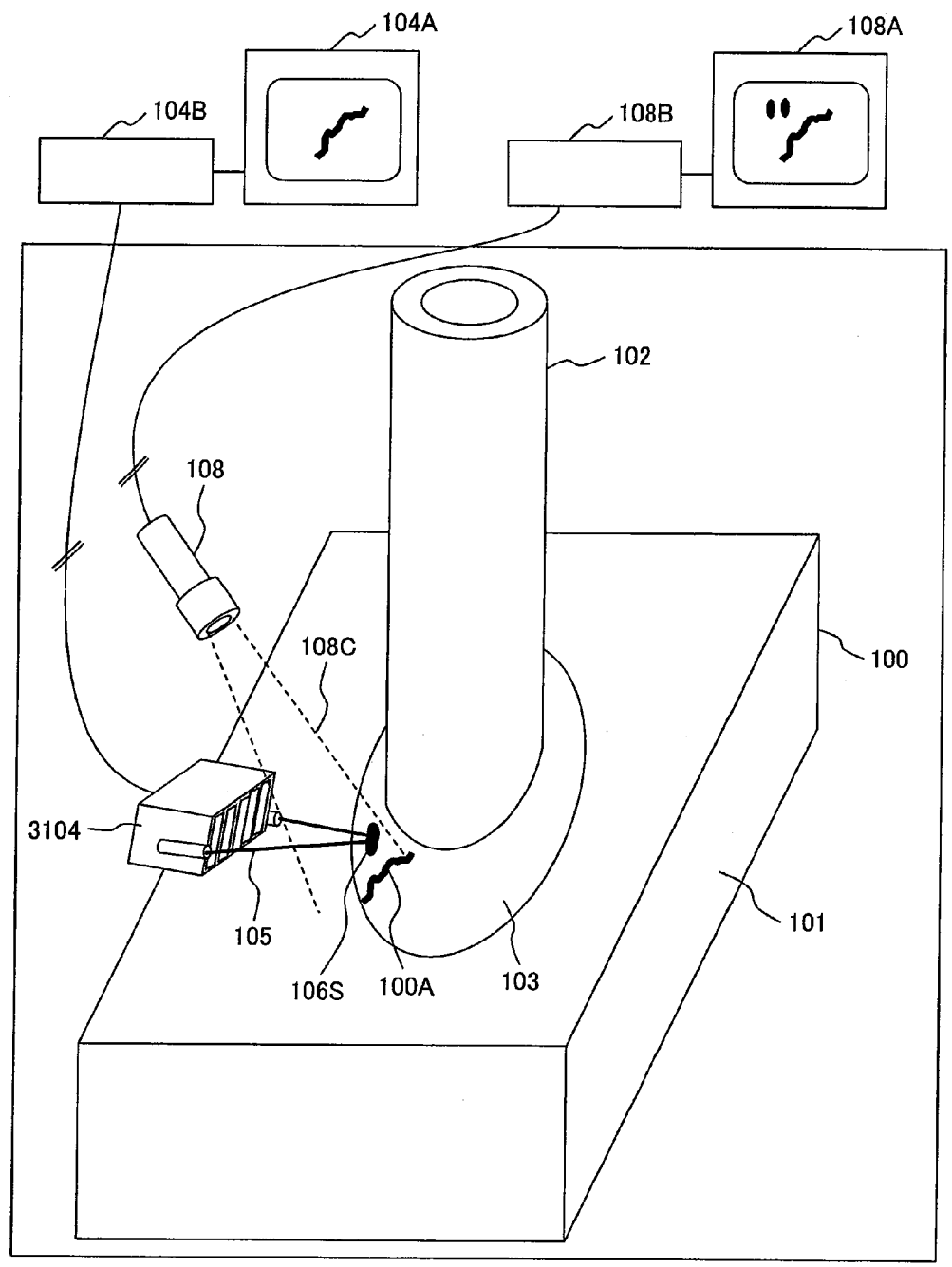
FIG. 28 is an illustrative diagram showing a configuration of an ultrasonic inspection system in accordance with an embodiment 7 of the present invention.

FIG. 28 shows a configuration of an ultrasonic inspection system in accordance with an embodiment 7 of the present invention. In the embodiment 7, an array transducer 3104 composed of plural transducers is adopted as an ultrasonic sensor.

Figure 29:
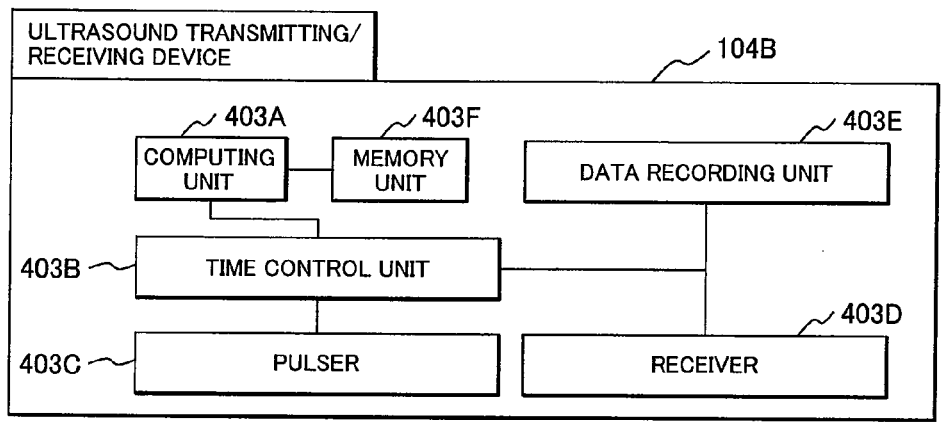
FIG. 29 is a diagram showing a configuration of an ultrasonic wave transmitting/receiving unit included in the embodiment 7 of the present invention.

Referring to FIG. 29, actions performed in the ultrasonic wave transmitting/receiving device 104B when the array transducer is employed will be described below. The ultrasonic wave transmitting/receiving device 104B includes a computing unit 403A, a time control unit 403B, a pulser 403C, a receiver 403D, and a data recording unit 403E. The pulser 403C feeds a driving signal to the array transducer 3104. The receiver 403D handles receiving signals inputted from the array transducer 3104.

The computing unit 403A controls the time control unit 403B, pulser 403C, receiver 403D, and data recording unit 503E so that necessary actions can be performed. In the embodiment 7, a delay pattern due to an acoustic velocity of a longitudinal wave in a liquid (water) that is a medium in which the array transducer 3104 is immersed, and patterns for a group of transmitting/receiving elements to be used to sequentially switch incident positions are stored in a memory unit 403F.

To begin with, the time control unit 403B controls the timing of a driving signal outputted from the pulser 403C, and also controls the timing at which the receiver 403D inputs a receiving signal. Further, the patterns for the group of elements employed in transmitting or receiving are sequentially switched so that the array transducer 3104 can act in a phased array mode. Thus, transmitting positions can be sequentially switched. The data recording unit 503E handles a receiving signal fed from the receiver 403D, and feeds the resultant signal to the acoustic image display device 104A.

Figure 30:
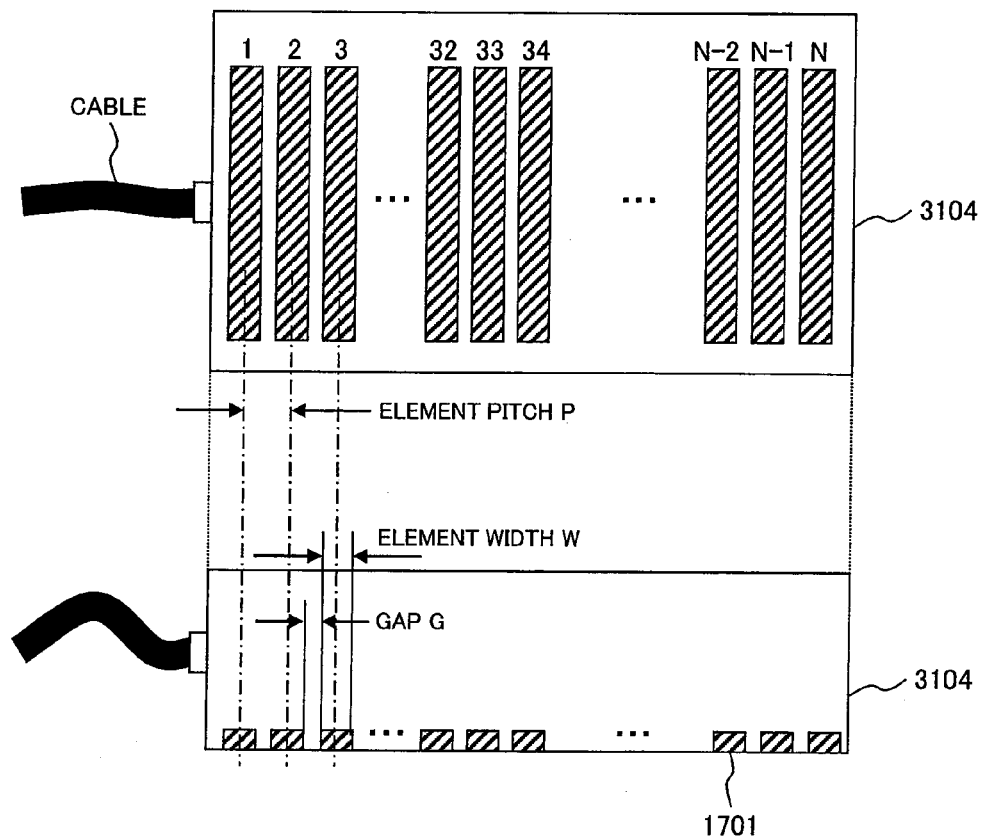
FIG. 30 is an illustrative diagram showing an array transducer included in the embodiment 7 of the present invention.

FIG. 30 shows a basic construction of the array transducer. The array transducer 3104 basically includes plural ultrasonic wave generation elements 1701. As the transmitting/receiving elements whose patterns are stored in the memory unit 403F, the ultrasonic wave generation elements 1701 constituting the array transducer 3104 are switched. For example, serial numbers ranging from 1 to N (N denotes, for example, 128) are assigned to the ultrasonic wave generation elements 1701. First, the first to thirty-second ultrasonic wave generation elements are selected. At the second step, the second to thirty-third ultrasonic wave generation elements are selected. At the third step, the third to thirty-fourth ultrasonic wave generation elements are selected. Thus, points from which ultrasonic waves originate can be sequentially shifted. Eventually, incident positions (incident points) on a steel product which the ultrasonic waves incident can be shifted.

Figure 31:
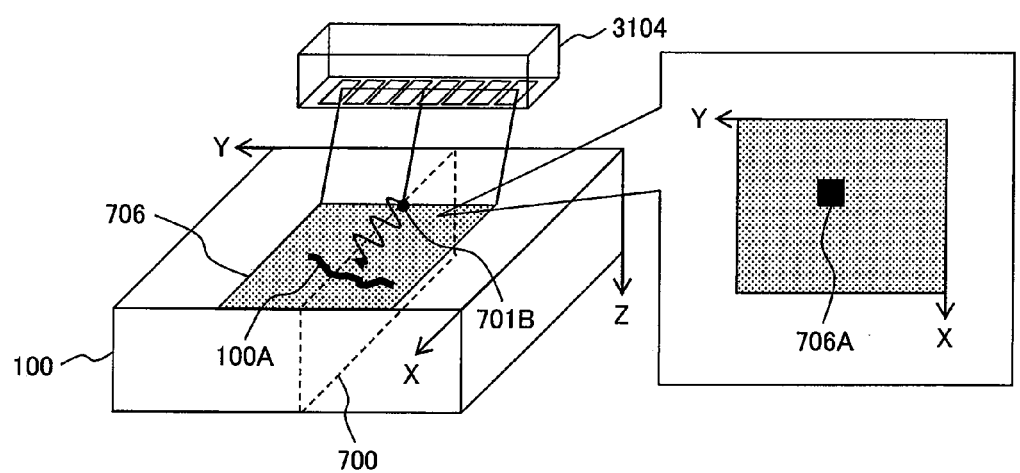
FIG. 31 is an explanatory diagram showing acoustic image production based on ultrasonic waves and employed in the embodiment 7 of the present invention.

A method of forming an acoustic image using ultrasonic waves is identical to that implemented in the embodiment 5. However, as shown in FIG. 31, the incident positions of ultrasonic waves are shifted through electronic scanning through which the array transducer 3104 is moved in the X direction and the elements of the array transducer included in the ultrasonic sensor 104 are switched in the Y direction. Eventually, a two-dimensional acoustic image of an XY plane can be obtained.

According to the embodiment 7, an array transducer is adopted as an ultrasonic sensor, and incident positions of ultrasonic waves can be checked. Further, a result of ultrasonic inspection performed on a section of an test object can be instantaneously imaged. Therefore, an acoustic image and an optical image can be quickly compared with each other. Eventually, the incident positions of ultrasonic waves can be readily identified. This provides an advantage that a load imposed on mechanical sweeping performed by the moving mechanism, which sweeps the ultrasonic sensor, can be lightened.

Embodiment 8

Figure 32:
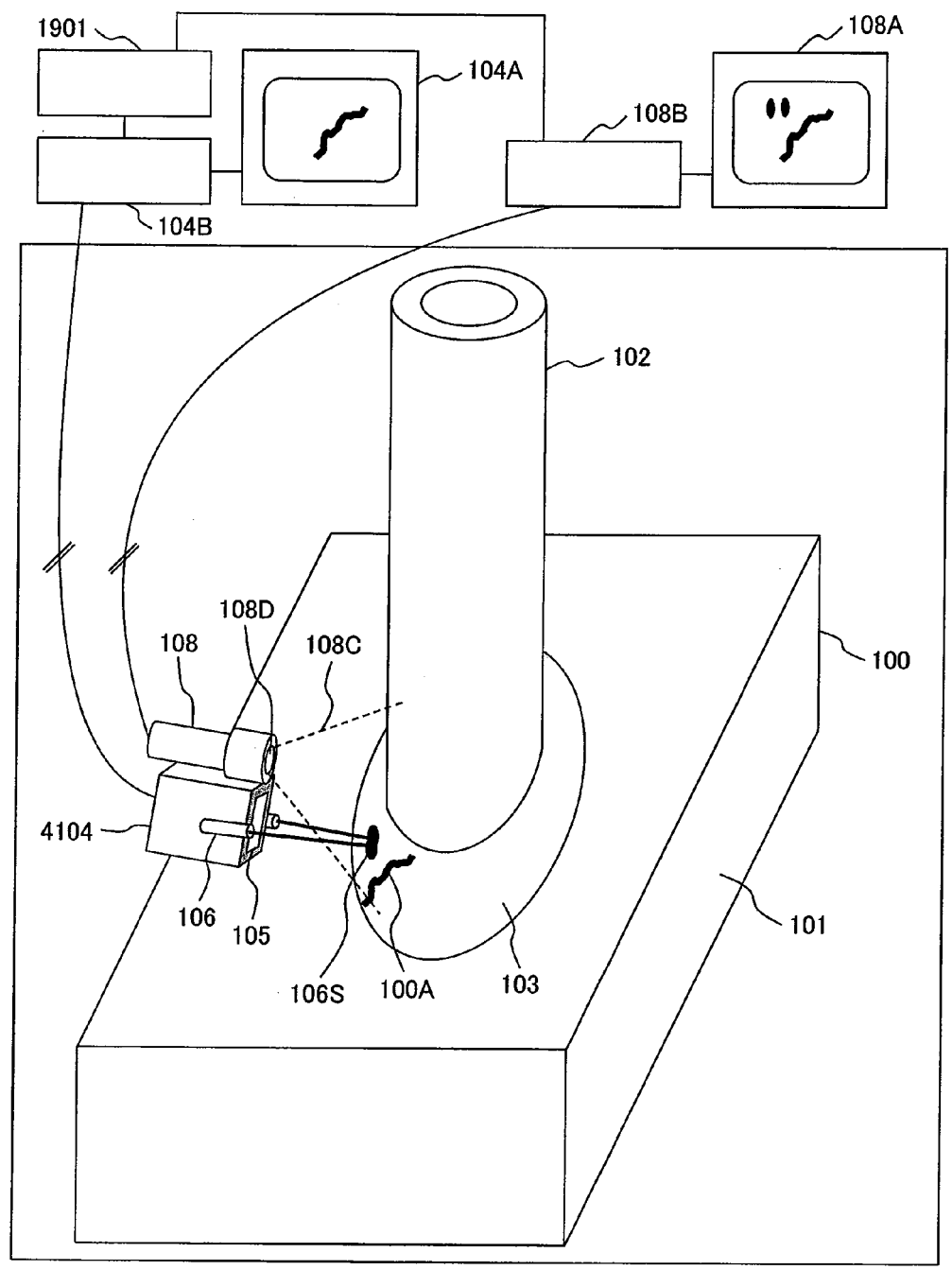
FIG. 32 is an illustrative diagram showing a configuration of an ultrasonic inspection system in accordance with an embodiment 8 of the present invention.

FIG. 32 shows a configuration of an ultrasonic inspection system in accordance with an embodiment 8. Laser markers serving as optical irradiators that irradiate an optical marker are mounted on an ultrasonic sensor 4104 serving as an ultrasonic wave transmitting/receiving unit. As the optical irradiator, aside from the laser marker, any unit capable of projecting an optical pattern such as a light bulb of visible light, an LED, or a liquid crystal projection will do.

The irradiated positions 106S on an test object of the optical markers and the test object 100 are imaged by, for example, an underwater camera 108 serving as imaging equipment. Reference numeral 108C denotes a field of view of the camera. An area on the test object 100 which an ultrasonic wave incidents or an area in which a reflected wave occurs is imaged.

Herein, the underwater camera 108 shall be mounted on the ultrasonic sensor 104, and shall include a lens 108D and an output unit that outputs an image dependent on the power of the lens. The ultrasonic sensor 104 is connected to the ultrasonic wave transmitting/receiving device 104B, and the image is displayed as information on a result of inspection on the acoustic image display device 104A. An image signal produced by the underwater camera 108 is fed to the camera controller 108B, and displayed as a pickup image on the optical image display device 108A.

One of the acoustic image and optical image can be selected and displayed for the purpose of collating the images with each other. The acoustic image and optical image may be synthesized by an image synthesis unit 1901, and the synthetic image can be displayed on the acoustic image display device or optical image display device.

Figure 33:
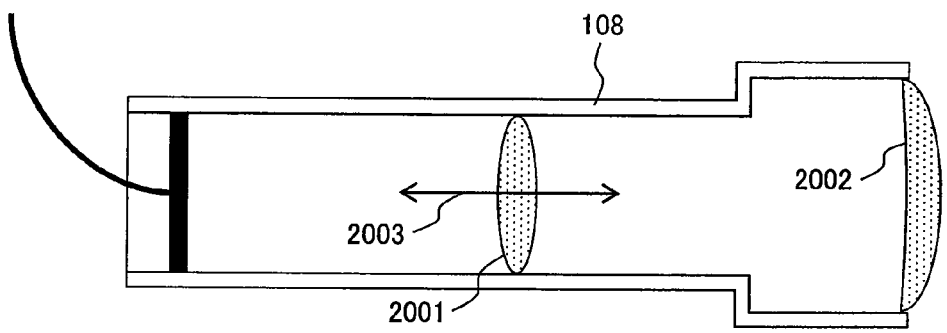
FIG. 33 is an illustrative diagram showing an underwater camera included in the embodiment 8 of the present invention.

FIG. 33 is a sectional view of the underwater camera 108. In the camera permitting a variable magnification, plural lenses, for example, a lens 2001 and a lens 2002 are incorporated. The magnification can be varied by shifting the position of the lens 2001. Therefore, the underwater camera 108 includes a mechanism, which drives the lens 2001 in a back-and-forth direction 2003, as the output unit that outputs an image enlarged or contracted according to the power of the lens. When images having different magnifications are outputted using the mechanism shown in FIG. 33, data items contained in optical images that are two-dimensionally recorded and obtained in plural fields of view can be converted into three-dimensional coordinates representing an imaged entity.

As described in relation to the embodiments 5 and 7, an acoustic image represented by three-dimensional data of X, Y, and Z coordinates can be obtained from the ultrasonic sensor.

Therefore, when the incident position of an ultrasonic wave is identified according to the embodiment 8, an acoustic image and an optical image can be displayed with the positions thereof superposed on each other.

Figure 34:
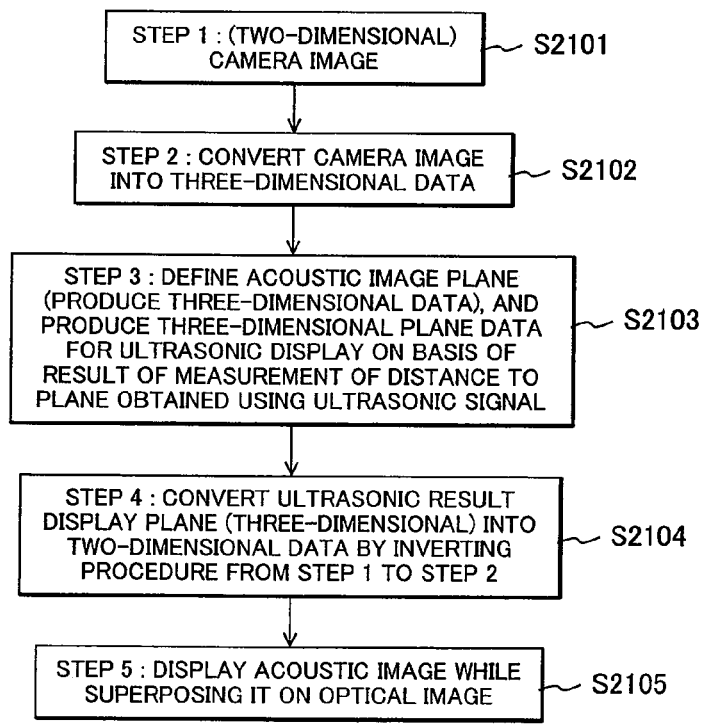
FIG. 34 is a flowchart of image synthesis employed in the embodiment 8 of the present invention.

FIG. 34 describes a processing flow. To begin with, (two-dimensional) optical images are picked up in plural fields of view by the camera (S2101).

Thereafter, the two-dimensional camera images are converted into three-dimensional data (S2102).

Further, as described in FIG. 34, a virtual acoustic image display plane is three-dimensionally set in the acoustic image, which is produced as the three-dimensional data, on the basis of a result of measurement performed on the distance between the ultrasonic sensor and test object (S2103).

Thereafter, the acoustic image represented by an ultrasonic wave is converted into an optical image of a two-dimensional plane by inverting coordinate transform that proceeds from the first step to the second step (S2104).

Figure 35:
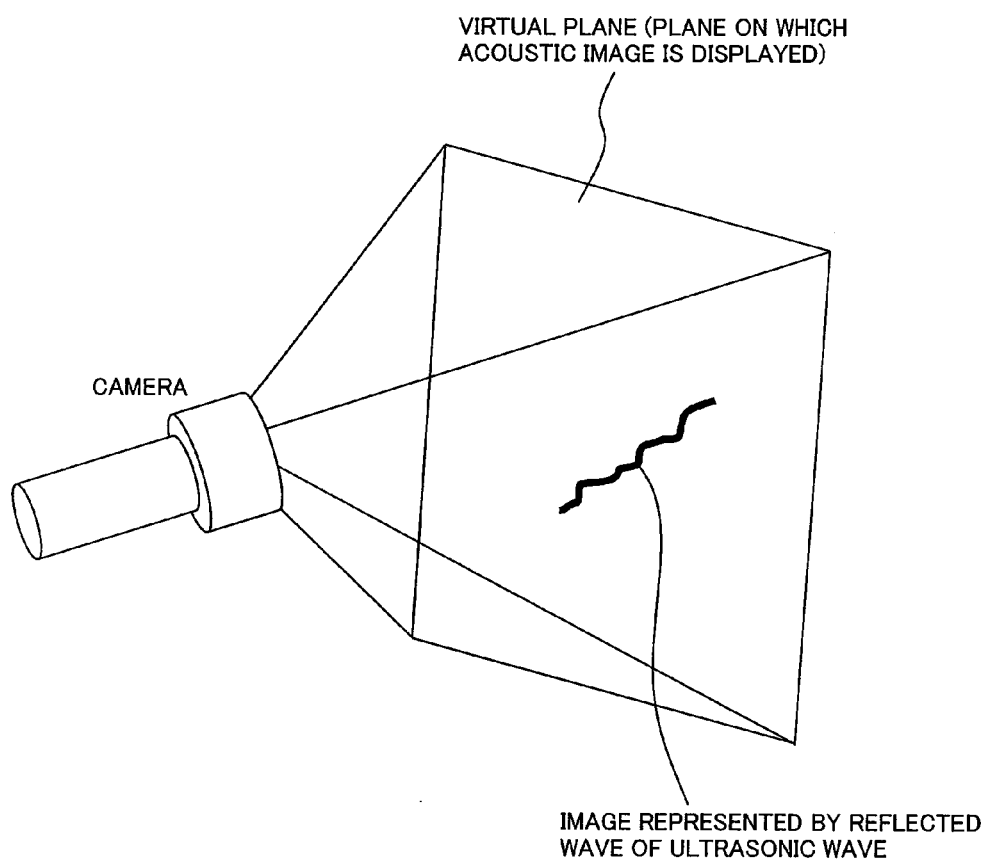
FIG. 35 is an illustrative diagram showing a virtual plane for the image synthesis employed in the embodiment 8 of the present invention.

Finally, as shown in FIG. 35, the acoustic image that has been transformed into a two-dimensional image is displayed while being superposed on the optical image obtained as a two-dimensional image.

As mentioned above, according to the embodiment 8, an advantage that an incident position of an ultrasonic wave can be identified is provided. Further, while the incident position of an ultrasonic wave emitted from an ultrasonic sensor as well as an test object is being imaged, inspection an be performed. Therefore, if a result of the ultrasonic inspection demonstrates a doubt of a defect, a situation of the inspection at the position concerned encompassing information on the surface of the test object can be checked. Otherwise, if the doubt of a defect is demonstrated by a visual inspection based on imaging, the result of the ultrasonic inspection can be checked at the position concerned. Eventually, a defect deciding ability and precision in dimension measurement can be improved.

What is claimed is:

1. An ultrasonic inspection system to be employed in ultrasonic inspection of a test object based on an immersion technique comprising:
   an ultrasonic sensor that emits or receives an ultrasonic wave, and which includes at least two lasers disposed such that optical axes of the lasers are tilted toward each other so that visible laser beams of the lasers intersect at a position separated by a predetermined distance from an ultrasonic wave emitting surface of the ultrasonic sensor;
   an ultrasonic inspection device that displays information on a result of inspection;
   a drive unit that is remotely controlled in order to move the ultrasonic sensor to a predetermined position on the test object;
   a laser that irradiates a laser beam on the test object; and
   imaging equipment that images the test object and a laser beam irradiated position, and which includes a camera,
   wherein a distance to a position at which the visible laser beams intersect is squared with a water distance required for the ultrasonic wave, which is emitted from the ultrasonic sensor, to become incident to the test object.

2. The ultrasonic inspection system according to claim 1, wherein the imaging equipment is a fiberscope that includes an illumination light source and the camera and images the test object.

3. An ultrasonic inspection method based on an immersion technique, comprising the steps of:
   mounting an ultrasonic sensor and a laser in a drive unit that is remotely controlled for driving, where the ultrasonic sensor includes at least two lasers disposed such that optical axes of the lasers are tilted toward each other so that visible laser beams of the lasers intersect at a position separated by a predetermined distance from an ultrasonic wave emitting surface of the ultrasonic sensor;
   irradiating a visible laser beam from the laser to an test object;
   imaging an irradiated position of the visible laser beam using imaging equipment including a camera; and
   performing inspection,
   wherein the distance to a position at which the visible laser beams intersect is squared with a water distance required for an ultrasonic wave, which is emitted from the ultrasonic sensor, to become incident with the test object.

4. The ultrasonic inspection method according to claim 3, wherein:
   the ultrasonic sensor and the fiberscope are mounted in a drive unit that is remotely controlled for driving; and
   the fiberscope is used to image the ultrasonic wave emitting direction in order to perform inspection.

5. An ultrasonic inspection system to be employed in ultrasonic inspection in which an ultrasonic wave is propagated to a test object via a medium such as a liquid or a gas, comprising:
   an ultrasonic wave transmitting/receiving unit that transmits or receives the ultrasonic wave;
   an acoustic image display device that displays information on a result of inspection;
   an optical irradiator that is mounted on the ultrasonic wave transmitting/receiving unit and irradiates an optical marker on the test object;
   imaging equipment that images the test object and an irradiated position of the optical marker; and
   an optical image display device that displays an image picked up by the imaging equipment,
   wherein the ultrasonic wave transmitting/receiving unit includes an ultrasonic array, the optical marker irradiated by the optical irradiator is a line shaped marker, and a direction of the ultrasonic array and a direction of the line shaped marker are parallel.

6. An ultrasonic inspection system to be employed in ultrasonic inspection in which an ultrasonic wave is propagated to a test object via a medium such as a liquid or a gas, comprising:
an ultrasonic wave transmitting/receiving unit that transmits or receives the ultrasonic wave;
an acoustic image display device that displays information on a result of inspection;
an optical irradiator that is mounted on the ultrasonic wave transmitting/receiving unit and irradiates an optical marker on the test object;
imaging equipment that images the test object and an irradiated position of the optical marker; and
an optical image display device that displays an image picked up by the imaging equipment,
wherein the ultrasonic wave transmitting/receiving unit includes an ultrasonic array, the optical marker irradiated by the optical irradiator is a line shaped marker, and a direction of the ultrasonic array and a direction of the line shaped marker perpendicularly cross.

7. The ultrasonic inspection system according to claims 5 or 6, wherein the imaging equipment is mounted on the ultrasonic wave transmitting/receiving unit.

8. The ultrasonic inspection system according to claims 5 or 6, wherein:
the optical irradiator mounted on the ultrasonic transmitting/receiving unit includes a plurality of optical irradiators; and
the optical irradiators irradiate a plurality of optical markers which intersect at a position separated by a predetermined distance from an ultrasonic wave emitting surface of the ultrasonic sensor.

9. The ultrasonic inspection system according to claims 5 or 6, wherein the imaging equipment includes a camera having a lens, and includes an output unit that outputs an image enlarged or contracted according to a power of the lens.

10. The ultrasonic inspection system according to claims 5 or 6, further comprising an image synthesis unit that synthesizes an acoustic image of the acoustic image display device and an optical image from the imaging equipment.

11. An ultrasonic inspection method in which an ultrasonic wave is propagated to a test object by an ultrasonic wave transmitting/receiving unit via a medium such as a liquid or a gas, comprising the steps of:
transmitting the ultrasonic wave to the test object;
A receiving a reflected wave, which returned from the surface of the test object or the interior thereof, as a received signal;
displaying an acoustic image as a result of inspection representing the received signal;
irradiating an optical marker on the surface of the test object;
imaging the test object and the optical marker using imaging equipment;
displaying a pickup image of the imaging equipment as an optical image; and
performing ultrasonic inspection,
wherein the ultrasonic wave transmitting/receiving unit includes a plurality of optical irradiators irradiating a plurality of the optical markers, a shape of each of the optical markers on the surface of the test object is a line, the optical irradiators are arranged so that the optical markers intersect, an angle at which the ultrasonic wave transmitting/receiving unit is disposed with respect to the test object is identified based on directions of the optical markers irradiated on the test object, and
wherein the ultrasonic wave transmitting/receiving unit includes an ultrasonic array, and a direction of the array arrangement of the ultrasonic array and a direction of one of the lines irradiated by the optical irradiators are parallel.

12. An ultrasonic inspection method in which an ultrasonic wave is propagated to a test object by an ultrasonic wave transmitting/receiving unit via a medium such as a liquid or a gas, comprising the steps of:
transmitting the ultrasonic wave to the test object;
receiving a reflected wave, which is returned from the surface of the test object or the interior thereof, as a received signal;
displaying an acoustic image as a result of inspection representing the received signal;
irradiating an optical marker on the surface of the test object;
imaging the test object and the optical marker using imaging equipment;
displaying a pickup image of the imaging equipment as an optical image; and
performing ultrasonic inspection,
wherein the ultrasonic wave transmitting/receiving unit includes a plurality of optical irradiators irradiating a plurality of the optical markers, a shape of each of the optical markers on the surface of the test object is a line, the optical irradiators are arranged so that the optical markers intersect, an angle at which the ultrasonic wave transmitting/receiving unit is disposed with respect to the test object is identified based on directions of the optical markers irradiated on the test object, and
wherein the ultrasonic wave transmitting/receiving unit includes an ultrasonic array, and a direction of the array arrangement of the ultrasonic array and a direction of one of the lines irradiated by the optical irradiators cross at right angles.

13. The ultrasonic inspection method according to claims 11 or 12, wherein:
the imaging equipment is used to perform optical inspection on the surface of the test object; and
the optical inspection and ultrasonic inspection are simultaneously or selectively carried out.

14. The ultrasonic inspection method according to claims 11 or 12, wherein:
an ultrasonic wave transmitting/receiving unit includes the optical irradiators;
the optical irradiators have optical axes which are tilted toward each other so that the optical markers intersect;
the shape of each of the optical markers on the surface of the test object is switchable to a spot;
the optical irradiators are arranged so that the plurality of optical markers as spots intersect at one point; and
the optical markers as spots are measured in order to identify the distance between the ultrasonic wave transmitting/receiving unit and test object.

15. The ultrasonic inspection method according to claims 11 or 12 wherein two or more optical irradiators mounted on the ultrasonic wave transmitting/receiving unit exhibit a plurality of irradiation patterns as the optical markers.

* * * * *